(12) United States Patent
Böhler et al.

(10) Patent No.: US 8,372,806 B2
(45) Date of Patent: Feb. 12, 2013

(54) TRANSDERMAL DELIVERY SYSTEM FOR TREATING INFERTILITY

(75) Inventors: Christof Böhler, Berneck (CH); Thomas Bragagna, Feldkirch (AT); Reinhard Braun, Lustenau (AT); Werner Braun, Lochau (AT); Herbert Zech, Bregenz (AT)

(73) Assignee: Pantec Biosolutions AG, Ruggell (LI)

( * ) Notice: Subject to any disclaimer, the term of this patent is extended or adjusted under 35 U.S.C. 154(b) by 23 days.

(21) Appl. No.: 12/089,445

(22) PCT Filed: Oct. 6, 2006

(86) PCT No.: PCT/EP2006/067159
§ 371 (c)(1),
(2), (4) Date: Apr. 7, 2008

(87) PCT Pub. No.: WO2007/039646
PCT Pub. Date: Apr. 12, 2007

(65) Prior Publication Data
US 2008/0255034 A1    Oct. 16, 2008

(30) Foreign Application Priority Data
Oct. 6, 2005 (EP) .................................. 05109298

(51) Int. Cl.
*A61K 38/00* (2006.01)
*A61K 38/24* (2006.01)
*A61K 50/00* (2006.01)

(52) U.S. Cl. ........ 514/9.8; 514/9.9; 514/10.1; 514/10.3; 424/449; 427/2.14; 427/2.31

(58) Field of Classification Search .................. None
See application file for complete search history.

(56) References Cited

U.S. PATENT DOCUMENTS

| 5,980,934 A | 11/1999 | Reber et al. |
| 2005/0163827 A1 * | 7/2005 | Zech et al. ............... 424/448 |

FOREIGN PATENT DOCUMENTS

| WO | 0069515 | 11/2000 |
| WO | 0074767 | 12/2000 |
| WO | 02092163 | 11/2002 |
| WO | 03068197 | 8/2003 |
| WO | WO03/077971 | * 9/2003 |
| WO | 2006/111199 | 10/2006 |

OTHER PUBLICATIONS

Nicoli et al., Pharmaceutical Research, 2001; 18: 1634-1637.*
Sharara and McClamrock, Human Reprod. 1999; 14: 2777-2782.*
Papanikolaou et al., Hum Reprod. 2008; 23:91-9.*

* cited by examiner

*Primary Examiner* — Bridget E Bunner
*Assistant Examiner* — Christina Borgeest
(74) *Attorney, Agent, or Firm* — Fish & Associates, P.C.

(57) ABSTRACT

The transdermal delivery system for treating infertility in a patient comprises an apparatus (10) for facilitating transdermal delivery of a drug (5*a*) through an area of the apparatus (10) comprises an ablator that is configured to generate a microporation in the area of the skin of the patient, and comprises a drug (5*a*), wherein the drug effects at least one of the biological regulation of at least one oocyte containing follicle, stimulation of follicle growth, induction of ovulation, promotion of gestational status, maintenance of conceptus, maintenance of pregnancy.

16 Claims, 18 Drawing Sheets

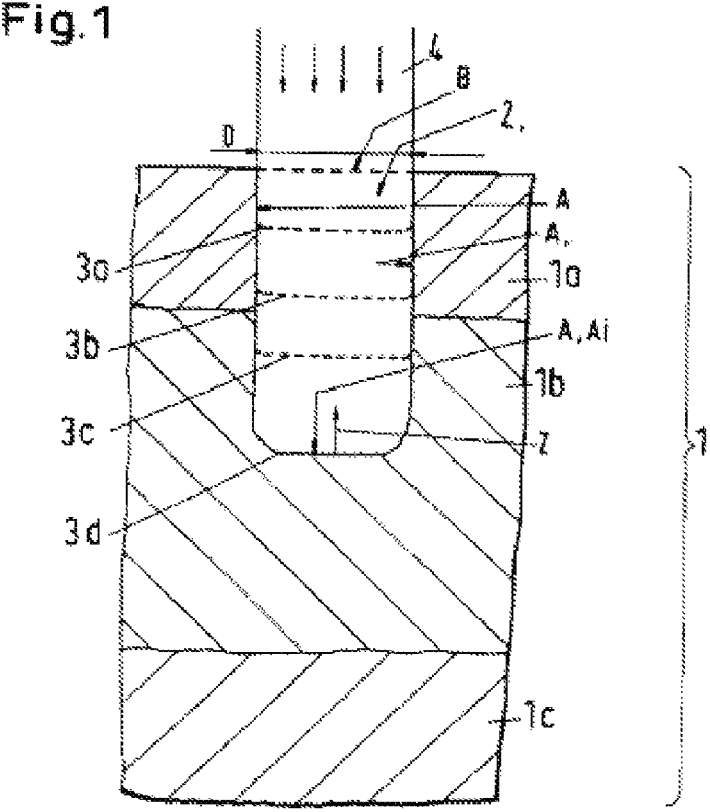
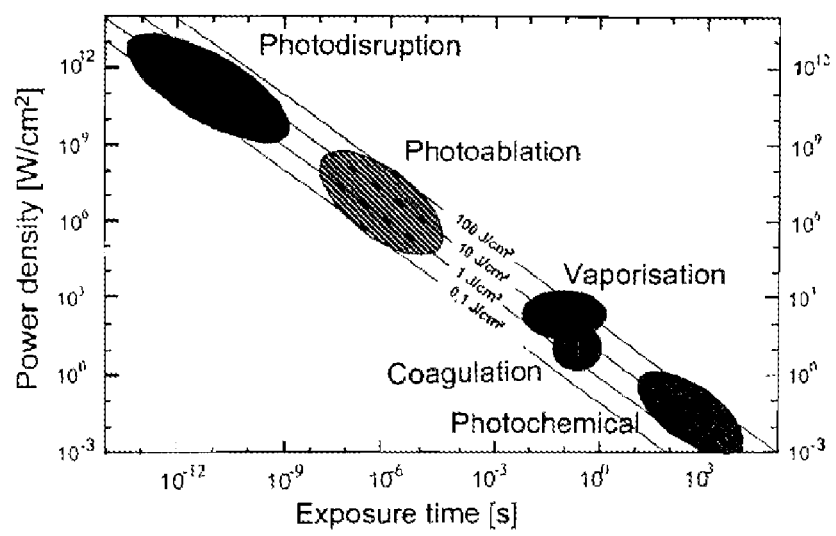
Fig. 1a

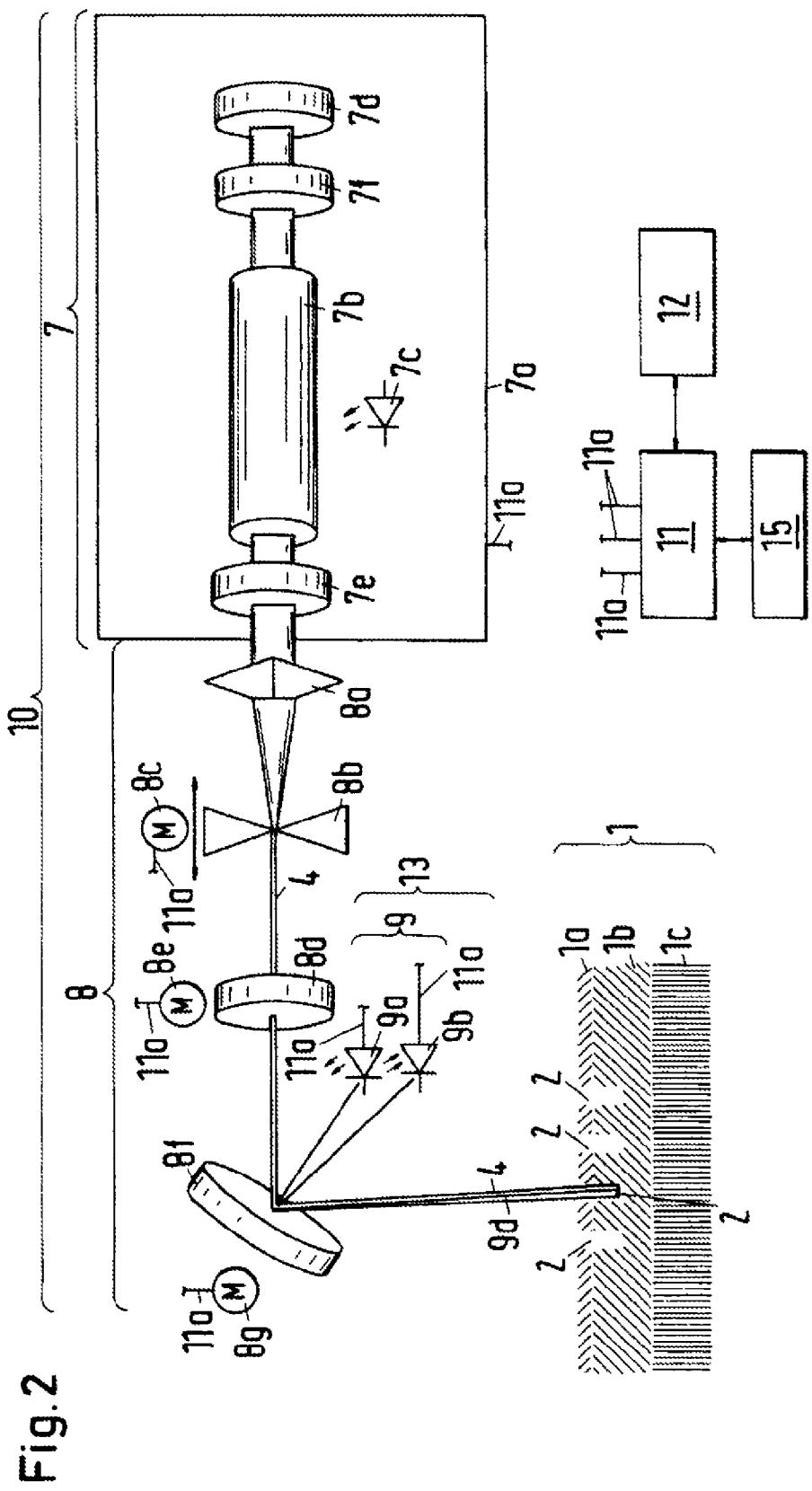

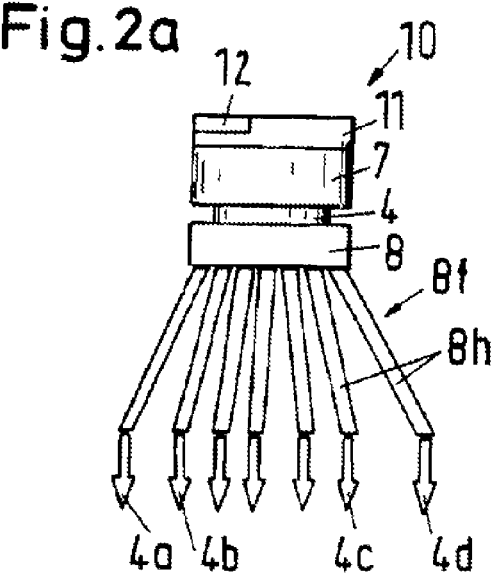
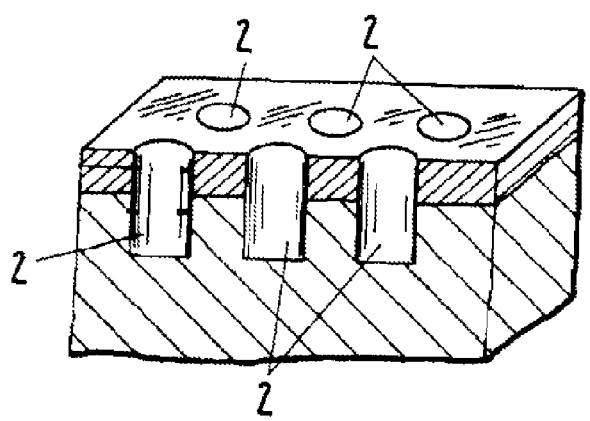
Fig. 3a
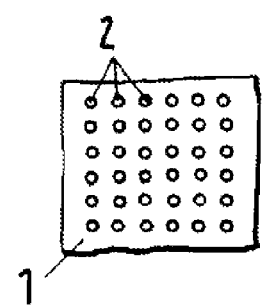
Fig. 3b

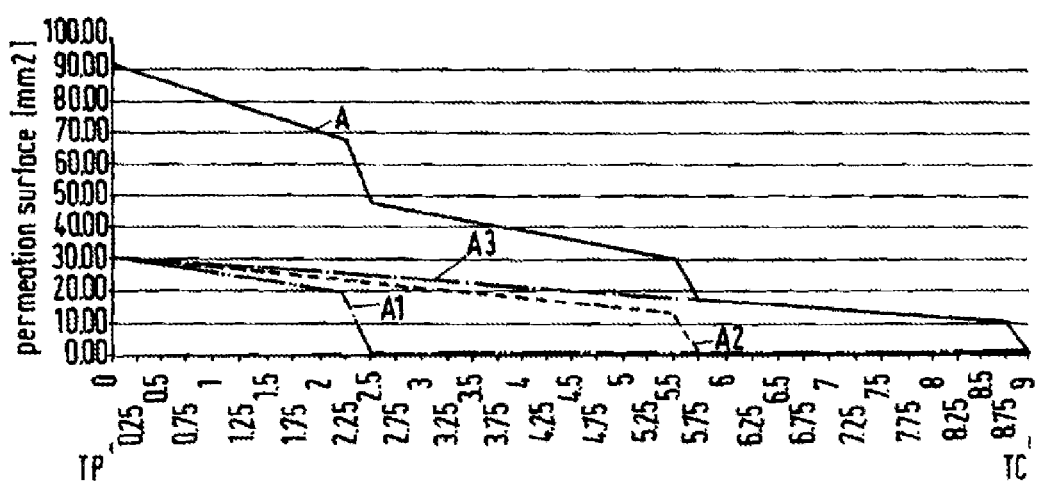

TRANSDERMAL DELIVERY SYSTEM FOR TREATING INFERTILITY

CROSS-REFERENCE TO RELATED APPLICATIONS

This application claims priority from EP Pat. Application No. 05109298.9, filed on Oct. 6, 2005 which is hereby incorporated by reference in their entirety.

FIELD OF THE INVENTION

This invention relates to an improved transdermal delivery system and a method of treating infertility.

BACKGROUND OF THE INVENTION

According to the American Society for Reproductive Medicine, 6.1 million people in the United States are affected by infertility. This number represents approximately 10% of the reproductive age population. One procedure used to overcome problems of infertility is in vitro fertilization (hereinafter designated IVF).

IVF of human oocytes (egg cells) has become commonly used for the treatment of female and male subfertility. The standard IVF treatment includes a long phase of hormone stimulation of the female patient, e.g. 30 days, which in most of the cases is initiated by suppressing the patient's own follicle stimulating hormone (hereinafter designated FSH) and luteinising hormone (hereinafter designated LH) by gonadotropin releasing hormone agonists (hereinafter designated GnRH-agonists), and this is followed by injections of exogenous gonadotropins, e.g. FSH and/or LH, in order to ensure development of multiple preovulatory follicle development and aspiration of multiple in vivo matured oocytes immediately before ovulation. The aspirated oocytes are subsequently fertilised in vitro and cultured, typically for two to five days before transferral back into the uterus at the 4 cell stage up to the blastocyst stage. After transferral progesterone is administered by intramuscular injection.

One object of the present invention is to treat human infertility.

Another object of the present invention is to improve the fertility, in particular the stimulation of the ovarian production of oocytes.

Another object of the present invention is to improve the implantation and subsequent pregnancy development.

Another object of the present invention is to improve the rate of implantation of oocytes by human in vitro maturation and fertilisation.

Another object of the present invention is to improve the sperm production and hormone production in men.

Another object of the present invention is to make the administration of substances such as hormones or drugs more comfortable and more reliable, in order to improve treatment of infertility.

Another object is to improve transdermal delivery systems.

SUMMARY OF THE INVENTION

The treatment of infertility usually requires a variety of different drugs to be administered, sometimes even during a relative long period of time, e.g. 30 days or more. The method of treating infertility in a patient usually comprises administration of a plurality of different drugs to effect at least one of the biological regulation of at least one oocyte containing follicle, the stimulation of the follicle growth, the induction of ovulation, the promotion of gestational status, the maintenance of conceptus and maintenance of the pregnancy. The method of treating infertility in a man usually comprises administration of at least one drug such as FSH or LH, to improve sperm production and/or hormone production in the testicles. It has now been found that drugs may be administered transdermally, even drugs with high molecular weight, or drugs needed in a high amount of for example up to 600 IU of FSH/LH per day or up to 100 mg of progesterone per day. If appropriate, poration of the skin is used to enhance the flow of the drug across the skin barrier. The poration allows administration of drugs even with a very high molecular weight, and also allows administration of drugs in high quantities. By predetermined poration parameters, the administered dosage of the drug may be determined. The poration parameters may be determined according to the patients' personal characteristics or needs, allowing to individually adjusting the dosage of the drug for each patient. Briefly, the present invention relates to a transdermal delivery system and a method for treating infertility in a patient, wherein poration is used to prepare the skin, and wherein the administration of the drug is transdermally. In the most advantageous embodiment, the poration is performed by using a laser, and the poration is performed to allow formation of a plurality of micropores.

A micro-porator for porating a biological membrane to create a poration may be designed, for example, as the laser micro-porator disclosed in PCT patent application No. PCT/EP2005/051704 of the same applicant, and entitled "Laser microporator and method for operating a laser microporator".

The biological membrane may be porated according to a method, for example, as disclosed in PCT patent application No. PCT/EP2005/051703 of the same applicant, and entitled "Method for creating a permeation surface".

A micro-porator for porating a biological membrane and an integrated permeant administering system may be designed, for example, as the micro-porator disclosed in PCT patent application No. PCT/EP2005/051702 of the same applicant, and entitled "Microporator for porating a biological membrane and integrated permeant administering system".

A system for transmembrane administration of a permeant and a method for administering a permeant may be designed, for example, as the system disclosed in PCT patent application No. PCT/EP2005/055061 of the same applicant, and entitled "A system for transmembrane administration of a permeant and method for administering a permeant".

All citations herein are assigned to the applicant of the present application and incorporated by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply The system, device and method according to the invention utilize a micro-porator for porating a biological membrane like the skin, to create a microporation. The microporation comprising a plurality of individual micropores or a plurality of microchannels. In a preferred embodiment a laser microporator is used. The micro-porator ablates or punctures the biological membrane, in particular the stratum corneum and part of the epidermis of the skin. This effects individual porations (micropores, microchannels) in the skin, which results in an increase in skin permeability to various substances, which allows a transdermal or intradermal delivery of substances applied onto the skin. A microporation comprising micropores and created by the micro-porator in one session comprises a plurality of individual micropores, having a total number in the range between 10 and 1 million individual micropores. By each individual micropore a permeation surface within the skin is created. Depending on the number and shape of the individual micropores a total initial permeation surface is created, which is the sum of the permeation surfaces of all individual micropores. Due to cell growth, the permeation surface of each individual micropore decreases over time, and therefore also the total permeation surface, which is the sum of the permeation surface of all individual micropores, decreases over time. The decrease of the permeation surface over time depends in particular on the geometrical shape of the individual micropore. By an appropriate choice of the number of individual micropores and their shape, not only the total initial permeation surface but also the decrease of the total permeation surface over time can be determined. The appropriate choice of number and shape can be calculated and stored as an initial microporation dataset. The system according to the invention has the ability to reproducibly create a microporation with a predetermined initial permeation surface and in a further embodiment also with a predetermined function of the total permeation surface over time. Any biological tissue, but in particular the skin, can be porated with a microporator according to the invention.

Various techniques can be used to porate biological tissues. Preferably a microporator using a laser beam for creating micropores is used. But, for example, also a device for heating via conductive materials can be used for creating micropores, or a device generating high voltage electrical pulses can be used for creating microchannels. U.S. Pat. No. 6,148,232, for example, disclose a technique for creating microchannels by using an electrical field. Among other reasons, the following reasons allow to create a very sophisticated poration using the laser microporator as herewith disclosed:

a) The laser microporator allows creating micropores, whereas the device using high voltage electrical pulses creates microchannels. The difference in geometry between a micropore or pore and a microchannel, for example in the skin, is that the micropore has a single opening at the surface of the skin and ends within the skin, whereas the microchannel has at least two spaced apart openings at the surface of the skin and a channel connecting the at least two openings.

b) The laser microporator allows creating micropores with reproducible geometrical parameters like shape, area and diameter of the cross section and preferably also depth and inner surface of the micropore, whereas the geometrical parameters of microchannels created by high voltage electrical pulses have a high variation and are therefore not so reproducible.

c) The laser microporator allows varying geometrical parameters and/or varying the total permeation surface of the created pores, which enables adaptation of the microporation according to specific needs such as individual needs or dosage.

d) The laser microporator allows, by selecting appropriate parameters, creating micropores with highly reproducible characteristics, so that the transdermal delivery of the drug through the permeation surface of the micropores is more reproducible and more predictable e) The laser microporator allows creating a permeation of micropores with a much higher total initial permeation surface per $cm^2$ skin surface, compared with microchannels, due to the fact that the openings of the micropores can be arranged denser on the skin than the openings of microchannels, and due to the fact that micropores can extend deeper into the skin than microchannels.

f) The laser microporator allows creating micropores with little irreversible tissue damage.

g) The laser microporator as well as devices and methods according to the inventive subject matter allow for precise and predetermined pore geometry, and thus providing a tool for control of drug delivery dynamic and kinetic. The amount of substances delivered through the biological membrane, in particular from the surface of the skin to within the animal, mammal or human body, depends on the permeation surface and its variation over time. The present invention therefore also provides a system for transmembrane administration of a permeant, to provide a permeant like a drug, to provide an appropriate initial microporation dataset, and to provide a micro-porator to create a microporation according to the initial microporation dataset. After the microporation is created, a permeant is applied onto the skin, and the transdermal or intradermal delivery of the permeant takes place in a predetermined way. To apply the permeant effectively, it is important to fit properties of the permeant and the microporation accordingly, to ensure a desired local or systemic effect, for example to ensure a predetermined concentration of a drug in the blood.

According to one preferred embodiment, the system allows, for a specific drug, to select an appropriate initial microporation dataset out of a plurality of initial microporation datasets, so that a microporation is created according to the appropriate initial microporation dataset. When the respective drug is applied onto the skin, the transdermal delivery of the drug in function of time is mainly determined by the function of the permeation surface over time. The integrated permeant administering system therefore also allows to individually apply a drug, and for example to reach a predetermined concentration of a drug in the blood according to individual needs. In a preferred embodiment and method, personalised parameters of the mammal or human are taken into account when choosing or calculating a personalised initial microporation dataset, so the permeant is administered on personalised needs, to for example ensure for an individual person an optimal, personally adapted concentration or level of a drug in the blood.

As used herein, blood level, serum concentration, concentration level means the level or concentration of the permeant at a specific location, for example in a tissue, liquid, organ. Amount means the total amount of the permeant at a specific location. Amount over time, concentration over time, concentration level over time, is the function of time of the amount or concentration level.

As used herein, "poration" or "microporation" means the formation of small holes or micropores or microchannels, preferably to a desired depth, in or through the biological membrane or tissue, such as the skin, the mucous membrane or an organ of a human being or a mammal, or the outer layer of an organism or a plant, to lessen the barrier properties of this biological membrane to the passage of permeants or drugs into the body. The microporation referred to herein shall be no smaller than 1 micron across and at least 1 micron in depth.

As used herein, "micropore", "pore" or "individual pore" or "microchannel" means an opening formed by the microporation method.

As used herein "ablation" or "poration" means the controlled removal of material which may include cells or other components comprising some portion of a biological membrane or tissue. The ablation can be caused, for example, by one of the following:

kinetic energy released when some or all of the vaporizable components of such material have been heated to the point that vaporization occurs and the resulting rapid expansion of volume due to this phase change causes this material, and possibly some adjacent material, to be removed from the ablation site;

laser beam;

Thermal or mechanical decomposition of some or all off the tissue at the poration site by creating a plasma at the poration site;

heating via conductive materials;

high voltage AC current;

pulsed high voltage DC current;

micro abrasion using micro particles;

pressurised fluid (air, liquid);

pyrotechnic;

Electron beam or ion beam;

The device causing the ablation or poration is herein called the ablator or porator or microporator.

As used herein, "tissue" means any component of an organism including but not limited to, cells, biological membranes, bone, collagen, fluids and the like comprising some portion of the organism.

As used herein "puncture" or "micro-puncture" means the use of mechanical, hydraulic, sonic, electromagnetic, or thermal means to perforate wholly or partially a biological membrane such as the skin or mucosal layers of a human being or a mammal, or the outer tissue layers of a plant.

To the extent that "ablation" and "puncture" accomplish the same purpose of poration, i.e. the creating a hole or pore in the biological membrane optionally without significant damage to the underlying tissues, these terms may be used interchangeably.

As used herein "puncture surface" means the surface of the hole or pore at the outer surface of the biological membrane, which has been ablated or punctured.

As used herein the terms "transdermal" or "percutaneous" or "transmembrane" or "transmucosal" or "transbuccal" or "transtissual" or "intratissual" means passage of a permeant into or through the biological membrane or tissue to deliver permeants intended to affect subcutaneous layers and further tissues such as muscles, bones. In the most preferred embodiment the transdermal delivery introduces permeants into the blood, to achieve effective therapeutic blood levels of a drug.

As used herein the term "intradermal" means passage of a permeant into or through the biological membrane or tissue to delivery the permeant to the dermal layer, to therein achieve effective therapeutic or cosmetic tissue levels of a permeant, or to store an amount of permeant during a certain time in the biological membrane or tissue, for example to treat conditions of the dermal layers beneath the stratum corneum.

As used herein, "permeation surface" means the surface of the tissue within the micropore or microchannel. "Permeation surface" may mean the surface of an individual micropore or microchannel, or may mean the total permeation surface, which means the sum of all individual surfaces of all individual micropores or microchannels.

As used herein, "corrected permeation surface" means the permeation surface corrected by a factor or a specific amount, for example by subtracting the surface of the micropore or pore which is part of the stratum corneum.

As used herein, the term "bioactive agent," "permeant," "drug," or "pharmacologically active agent" or "deliverable substance" or any other similar term means any chemical or biological material or compound suitable for delivery by the methods previously known in the art and/or by the methods taught in the present invention, that induces a desired effect, such as a biological or pharmacological effect, which may include but is not limited to (1) having a prophylactic effect on the organism and preventing an undesired biological effect such as preventing an infection, (2) alleviating a lack or excess of substances (e.g. vitamins, electrolytes, etc.), (3) alleviating a condition caused by a disease, for example, alleviating pain or inflammation caused as a result of disease, (4) either alleviating, reducing, or completely eliminating the disease from the organism, and/or (5) the placement within the viable tissue layers of the organism of a compound or formulation which can react, optionally in a reversible manner, to changes in the concentration of a particular analyte and in so doing cause a detectable shift in this compound or formulation's measurable response to the application of energy to this area which may be electromagnetic, mechanical or acoustic. The effect may be local, such as providing for a local anaesthetic effect, or it may be systemic.

Such substances include broad classes of compounds normally delivered into the organism, including through body surfaces and membranes, including skin as well as by injection, including needle, hydraulic, or hypervelocity methods. In general, this includes but is not limited to: Polypeptides, including proteins and peptides (e.g., insulin); releasing factors, including Luteinizing Hormone Releasing Hormone (LHRH), Luteinizing Hormone (LH); follicle stimulating hormone (FSH); human chorionic gonadotropin (HCG); human growth hormone (HGH); Botulinum Toxin; carbohydrates (e.g., heparin); nucleic acids; vaccines; and pharmacologically active agents such as antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol, testosterone, progesterone and other steroids and derivatives and analogs, including corticosteroids; hypnotics; immunosuppressives; muscle relaxants; parasympatholytics; psychostimulants; sedatives; and tranquilizers. By the method of the present invention, both ionized and nonionized permeants may be delivered, as can permeants of any molecular weight including substances with molecular weights ranging from less than 10 Daltons to greater than 1,000,000 Daltons.

As used herein, an "effective" amount of a permeant means a sufficient amount of a compound to provide the desired local or systemic effect and performance at a reasonable benefit/risk ratio attending any treatment.

As used herein, "carriers" or "vehicles" refer to carrier materials without significant pharmacological activity at the quantities used that are suitable for administration with other permeants, and include any such materials known in the art, e.g., any liquid, gel, solvent, liquid diluent, solubilizer, microspheres, liposomes, microparticles, lipid complexes, or the like, that is sufficiently nontoxic at the quantities employed and does not interact with the drug to be administered in a deleterious manner. Examples of suitable carriers for use herein include water, buffers, mineral oil, silicone, inorganic or organic gels, aqueous emulsions, liquid sugars, lipids, microparticles and nanoparticles, waxes, petroleum jelly, and a variety of other oils, polymeric materials and liposomes.

As used herein, a "biological membrane" means a tissue material present within a living organism that separates one area of the organism from another and, in many instances, that separates the organism from its outer environment. Skin and mucous and buccal membranes are thus included as well as the outer layers of a plant. Also, the walls of a cell, organ, tooth, bone, finger nails, toe nails, cartilage or a blood vessel would be included within this definition.

As used herein, "transdermal flux rate" is the rate of passage of any bioactive agent, drug, pharmacologically active agent, dye, particle or pigment in and through the skin separating the organism from its outer environment. "Transmembrane flux rate" refers to such passage through any biological membrane.

The term "individual pore" as used in the context of the present application refers to a micropore or a pore, in general a pathway extending from the biological membrane. The biological membrane for example being the skin, the individual pore then extending from the surface of the skin through all or significant part of the stratum corneum. In the most preferred embodiment the pathway of the individual pore extending through all the stratum corneum and part of the epidermis but not extending into the dermis, so that no bleeding occurs. In the most preferred embodiment the individual pore having a depth between 10 µm (for newborns 5 µm) and 150 µm.

As used herein the term "initial microporation" refers to the total number of pores created. "Initial microporation dataset" refers to the set of data, wherein the initial microporation is defined. The dataset including at least one parameter selected from the group consisting of: cross-section, depth, shape, permeation surface, total number of individual pores, geometrical arrangement of the pores on the biological membrane, minimal distance between the pores and total permeation surface of all individual pores. Preferably the initial microporation dataset defines the shape and geometrical arrangement of all individual pores, which then will be created using the microporator, so that the thereby created initial microporation is exactly defined and can be reproduced on various locations of the biological membrane, also on different objects, subjects or persons. Even though the initial microporation is exactly defined by the initial microporation dataset, this doesn't mean that the initial microporation created in the biological membrane has the exact features as defined by the initial microporation dataset. For example, if the initial microporation dataset only defines the total number of individual pores, lets say 100, the initial microporation in the biological membrane will most probably comprise 100 individual pores. If the initial microporation dataset for example also defines the depth, shape or permeation surface, the initial microporation will most probably not have the exact geometrical parameters as defined with the initial microporation dataset, but the geometrical parameters will be in a certain range. The micro-porator may comprise feedback means, which scan the created pores, so the parameters of the created initial microporation can be measured and afterwards are known. Based on the feedback, the created pores may also be reshaped by the micro-porator, so the finally created pores respectively the initial microporation becomes more similar to the pores as defined by the initial microporation dataset.

The present invention employs a micro-porator comprising a controller, an initial microporation dataset and an ablator for creating a microporation, the controller reading the initial microporation dataset, and the controller controlling the ablator based on the initial microporation dataset and feedback device to create a microporation as defined by or similar to the initial microporation dataset. Thereby a microporation is created with a predetermined initial permeation surface, and preferably also with a predetermined permeation surface over time.

The ablator can be built in various ways, using various techniques. The ablator can for example comprise of mechanically driven needles. The needles may be heated to ablate the biological membrane by heating. In the most preferred embodiment a pulsed laser beam is used to create individual pores. In a preferred embodiment, the laser microporator applies a parallel or quasi-parallel laser beam on the biological membrane, which facilitates control over the precise shape of the individual pore. The term "parallel or quasi-parallel laser beam" used herein refers to a laser beam that has a divergence of less than 3°, at least within a certain range of focus, the focus or focus range, extending in direction of the propagation direction of the laser beam, is a range of about 1 cm to 5 cm, preferably a range of 2 cm to 3 cm. The laser micro-porator using a parallel or quasi-parallel laser beam, allows creation of individual pores with highly reproducible permeation surfaces. In the preferred embodiment the laser micro-porator comprises a feedback loop which is operatively coupled to the poration controller that actuates the laser source. The poration controller compares the measured characteristic of an individual pore with a predetermined value and stops emitting further laser pulses on the individual pore if the characteristic of the individual pore corresponds to the preset value, or if the characteristic of the individual pore is within a preset range. Most preferred the depth of the individual pore is monitored. This allows creation of an individual pore similar to drilling a hole in a material, in that the depth of the whole e.g. the pore is repeatedly measured. This allows to very accurately microporate a biological membrane so that the created microporation preferably corresponds to the predetermined values of the initial microporation dataset. In a preferred embodiment the laser microporator creates about the same increase in depth by pulse. By counting the amount of pulses per pore, an estimate of the total depth of the pore may be calculated.

The plurality of laser pulses applied onto the same pore allows creating individual pores having a reproducible shape of the wall surrounding the individual pore and preferably allows also creating a reproducible shape of the lower end of the individual pore. The inventor has found in at least some instances that the surface of the wall and the lower end have substantial influence on drug delivery rate, in particular the sum of the surface of the wall and the surface of the lower end which are part of the epidermis or the dermis, because this sum of surfaces forms a permeation surface through which most of the permeate passes into the tissue, for example into the epidermis and the dermis.

In a further embodiment the micro-porator is able to detect the depth at which the stratum corneum ends, e.g. the epidermis starts, for example, by using a spectrograph. This allows measuring the thickness of the stratum corneum and for example altering the total depth of created pores. With the initial microporation dataset, also the final depth of each individual pore may be defined. This final depth can now be corrected in that the thickness of the stratum corneum is added. The individual pore is then created with this corrected depth, which means the individual pore becomes deeper, and which means that the permeation surface of the epidermis corresponds to the given permeation surface. This is of importance, because the transdermal flux rate, depending on the drug applied, often depends on the size of permeation surface which allows a high passage of drugs, which might be the permeation surface of the epidermis only.

If the depth of the individual pore is not corrected by the thickness of the stratum corneum, the effect of the stratum corneum can be considered by calculating a corrected permeation surface. This corrected permeation surface for example comprising only the permeation surface of the epidermis. The total permeation surface of all individual pores can also be determined. Knowing the corrected permeation surface, which means the permeation surface of the epidermis, allows one to better control or predict the transdermal delivery of drug into the patient, e.g. to better control or predict the release of the drug into the patient.

The micro-porator can create a microporation having a number of individual pores in the range between 10 and up to 1 million, and having individual pores with a width between 0.01 and 0.5 mm, and a depth between 5 μm and 200 μm, as defined by the initial microporation dataset. The width of an individual pore may be constant or vary.

In a preferred embodiment the micro-porator comprises an interface to at least read the initial microporation dataset, and to preferably read further parameters like permeant information, user information or porator application information. In a further preferred embodiment the micro-porator comprises a database that stores a plurality of initial microporation datasets. In a further preferred embodiment the micro-porator comprises a selector, which manually or automatically selects, generates or modifies, for example based on personalised user information such as the age, the most appropriate initial microporation dataset, which then becomes the personalised initial microporation dataset. The pores are then created according to this most appropriate personalised initial microporation dataset.

The micro-porator can also comprise an inhibitor which inhibits the porator from porating if certain conditions are not fulfilled.

The micro-porator according to the invention allows creating on a biological membrane a wide variety of different, reproducible microporations, such as a wide variety of initial permeation surfaces and such as a wide variety of decreases of the permeation surface over time. The permeation surface affects the transdermal or intradermal delivery of the permeant like the drug. Therefore even the same drug or the same amount of drug applied onto the skin can be delivered differently into the skin, depending on the permeation surface. According to the invention an integrated permeant administering system is proposed, which considers relevant parameters regarding the permeant, the initial microporation dataset and the micro-porator, so that, after microporating the skin and after applying the drug onto the skin, the drug is released as requested into the skin, so that, for example, a defined blood-level profile is achieved.

After the poration is completed, a substance such as a drug is applied onto the skin, preferably in form of a transdermal patch, also called skin patch (for example under occlusion) or another delivery device. The transdermal patch offers a variety of significant clinical benefits over other dosage forms. Because passive as well as active transdermal patches deliver a predetermined drug concentration, and because the permeation surface over time being known, the transdermal patch offers controlled release of the drug into the patient, which for example enables a defined blood-level profile, resulting in reduced systemic side effects and, sometimes, improved efficacy over other dosage forms. In addition, transdermal patches are user-friendly, convenient, painless, and offer multi-day dosing. Transdermal patches therefore offer improved patient compliance. A substance can also be applied for cosmetic purpose only, for example applied intradermal.

BRIEF DESCRIPTION OF THE DRAWINGS

The present invention can be better understood and its advantages appreciated by those skilled in the art by referencing to the accompanying drawings, which are incorporated herein by reference. Although the drawings illustrate certain details of certain embodiments, the invention disclosed herein is not limited to only the embodiments so illustrated. Unless otherwise apparent from the context, all ranges include the endpoints thereof.

FIG. 1 shows a schematic cross-section of one pore of a laser porated skin;

FIG. 1a shows a map of laser-tissue interactions;

FIG. 2 shows a laser micro-porator device;

FIG. 2a shows a further micro-porator device;

FIG. 3a shows a perspective view of a micro-poration of the skin;

FIG. 3b shows a plan view of the skin with an array of micro-porations;

FIG. 4 shows the permeation surface of all micropores over time;

DETAILED DESCRIPTION

Figure 1B:
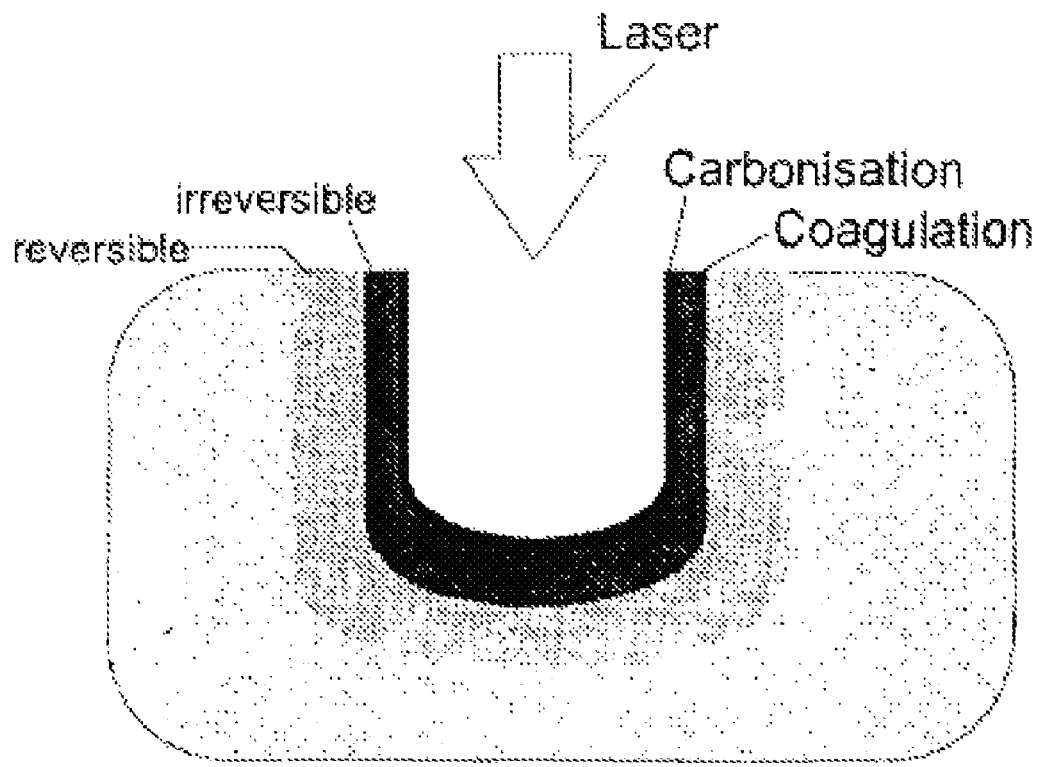
FIG. 1b shows a further cross-section of one pore of a laser porated skin.

FIG. 1 shows a cross-sectional view of the top layers of the biological membrane 1, a human skin, including a stratum corneum 1a, an epidermal layer or epidermis 1b and a dermal layer or dermis 1c. Underlying the stratum corneum 1a is the viable epidermis or epidermal layer 1b, which usually is between 50 and 150 μm thick. The epidermis contains no blood vessels and freely exchanges metabolites by diffusion to and from the dermis 1c, located immediately below the epidermis 1b. The dermis 1c is between 1 and 3 mm thick and contains blood vessels, lymphatics and nerves. Once a drug reaches the dermal layer, the drug will generally perfuse through system circulation.

FIG. 1 also shows a parallel or quasi-parallel laser beam 4 having a circular shape with a diameter D and acting on the surface of the skin 1. The impact of the laser beam 4 onto the skin 1 causes an ablation of the tissue. A first shot of the laser beam 4 causes an individual pore 2 with a lower end 3a. The first shot effecting a puncture surface B at the outer surface of the skin 1 in the size of about $(D/2)^2 *\pi$, which corresponds to the amount of the outer surface of the biological membrane, which has been ablated or punctured. A second shot of the laser beam 4 at the same location causes an increase in depth of the individual pore 2 up to the lower end 3b, and a third and forth shot at the same location causes a further increase in depth up to the lower ends 3c and 3d. The total surface of the tissue 1 surrounding the individual pore 2 corresponds to the permeation surface A. There is no tissue 1 at the puncture surface B, therefore the puncture surface B is not part of the permeation surface A.

Each individual pore 2 of the epidermis 1b has a cell growth of usually (untreated) 3 to 15 μm per day, the cells usually growing from the lower end of the individual pore 2 in direction Z to the stratum corneum 1a. Which means the lower end 3d of the individual pore 2 is moving into the direction of the stratum corneum with a speed of about 3 to 15 μm/day, thereby reducing the permeation surface A. The corrected permeation surface, being the permeation surface of the epidermis 1b only, without the surface of the stratum corneum 1a, becomes the size of the puncture surface, which means the surface of the hole in the stratum corneum, as soon as the cells have reached the stratum corneum 1a. The remaining hole in the stratum corneum 1a will by the time be filled by death cells of the epidermis, which significantly increases the barrier properties in the remaining hole, and which regenerates the stratum corneum. At the end the individual pore 2 has vanished due to cell growth, and the formerly ablated tissue is regenerated by new cells.

Depending on the type and operating conditions of the laser as well as on the tissue type and tissue exposure time, laser irradiation will produce a wide variety of effects. For example, and among other factors, the wavelength, pulse time/exposure time, energy density, power density, and focal spot size of the laser will, in combination with optical (e.g., reflection, absorption, scattering) and thermal (e.g., heat conduction and heat capacity) tissue properties determine the effect of the laser irradiation on a biological tissue.

FIG. 1a illustrates four exemplary categories of interactions (photochemical interaction, thermal interaction (vaporisation or coagulation), photoablation, and photodisruption) which are depicted in the graph as a function of irradiance or power density (W/cm$^2$), tissue exposure time (s), and energy dose (J/cm$^2$). The four diagonals in the graph show selected and constant energy doses at 0.1 J/cm$^2$ to 100 J/cm$^2$. Of course, it should be recognized that numerous other energy doses could also be depicted and be deemed suitable for use in conjunction with the teachings herein.

With respect to suitable laser types and operational parameters, it is generally contemplated that the laser type and operational parameters are selected such that photoablation and/or photodisruption is achieved at little or no irreversible tissue damage.

Therefore, preferred wavelengths of lasers used herein will predominantly have a wavelength in which water has a high absorbance and in which structural or functional components of the cell have significantly less or even no absorbance. Thus, contemplated wavelengths typically include mid-infrared and higher wavelengths, and especially preferred wavelengths will be in the range of between about 2500 nm and 5000 nm. Most preferred laser wavelengths are presently contemplated to be at about 3000 nm, and a person of ordinary skill in the art will be readily able to select suitable laser devices (e.g., Er:YAG laser with 2940 nm wavelength or Optical Parametric Oscillators (OPO)). Furthermore, and while not limiting to the inventive subject matter, the wavelength will preferably also be selected such that a minimum thermal destructive effect is achieved when the pulse time is 1 ms or less. Based on previous experiments (data not shown), thermal tissue damage is minimized at a wavelength of about 3000 nm where the pulse time was less than 100 μs, and more typically about 10 μs. A similar minimum was observed at wavelengths between 190 and 300 nm, however, such wavelengths are not suitable due to the high absorption of such radiation in the purine and pyrimidine bases of nucleic acids and aromatic residues of certain amino acids.

With respect to suitable ranges of irradiance it is generally preferred that the irradiance is at least $10^4$ W/cm$^2$, and more preferably at least $10^5$ W/cm$^2$, even more preferably between $10^5$ W/cm$^2$ and $10^9$ W/cm$^2$, and most preferably between $10^5$ W/cm$^2$ and $10^{12}$ W/cm$^2$ where energy doses of between about 0.01 J/cm$^2$ to 1000 J/cm$^2$, and more typically 0.1 J/cm$^2$ to 100 J/cm$^2$ are employed. Consequently, the laser pulse time/tissue exposure time is preferably less than 1 ms, more preferably less than 100 μs, even more preferably between 100 μs and 10 ns, and most preferably between 100 μs and 0.1 ps. Sizing and operation of lasers to achieve such parameters is well understood in the art, and many of the lasers and control systems therefore are commercially available.

With respect to suitable pulse times, and especially where relatively small laser pulse time/tissue exposure times are used, it should be noted that the laser parameters are preferably set such as to still achieve a blow-off effect (i.e. vaporization of tissue to a degree effective to thermally remove vaporized tissue). The person of ordinary skill in the art will readily appreciate that there is a positive correlation between irradiance and blow-off effect and a negative correlation between exposure time and depth of pore formation. Consequently, and particularly where small laser pulse time/tissue exposure times are used, multiple laser pulses onto the same pore, as disclosed in FIG. 1, will typically be required to form a micropore rather than to increase irradiance as such increase may also increase incidence of irreversible tissue damage (e.g., carbonization and/or coagulation). Consequently, and viewed from another perspective, it should be recognized that especially suitable operational parameters will be selected to provide a balance between minimum tissue damage and maximum desired effect. FIG. 1b discloses a further schematic cross-section on one micropore, showing irreversible tissue damages (carbonisation and coagulation) as well as reversible tissue damages. Selecting the operational parameters of the laser such that photoablation and/or photodisruption is achieved leads to a micropore with no or neglectable carbonisation and small irreversible tissue. To achieve a small amount of irreversible tissue is very important, because after healing, the tissue should be free of scars, in particular if the tissue, or even the same spot on the tissue, is repeatedly porated during a longer period of time such as some days or weeks.

Most preferably the pulsed beam having a wavelength between 2.65 microns and 3.1 microns, because water has a high absorption coefficient within this range. Most preferably the diameter of the beam is of less than 1 mm, so the needed energy per pulse is just high enough to stay above the ablation threshold of for example 1 Joule per square cm for human skin. Preferably pulses having a pulse time or temporal width of less than 1 μs are used, more preferably between 50 ns and 150 ns. Such a temporal width reduces the thermal damage of tissue surrounding a micro pore to a minimum because of the thermal relaxation time of water and biological tissue at wavelengths at 3 microns is about 1 μs. So heat conduction in the skin is very low and only given by very high pulse repetition rates due to heat accumulation. A temporal width of less than 150 ns further reduces the heating of tissue surrounding a micro pore also at high pulse repetition rates. Thermal relaxation is the process by which heat diffuses through tissue or water by conduction. When the laser exposure is less than the thermal relaxation time there is minimal thermal damage because most of the laser energy is converted into ablation energy. The thermal relaxation time of skin could be around 1 ms depending on the water content, and the thermal relaxation time of water could be around 1 μs. If laser light of such pulse length or longer would be applied to tissue, a high thermal transfer of heat would occur to the surrounding tissue. Because of the short pulses applied, which in a preferred embodiment are below the thermal relaxation time of skin or water, the tissue is less or even not damaged. To create an initial microporation on the biological membrane, the initial microporation preferably comprising between 100 and 10000 individual pores. The pulse repetition frequency of the laser source is preferably higher than 200 Hz, most preferably higher than 1 kHz. This means that the total time to create the entire initial microporation needs preferably less than 10 seconds.

FIG. 2 shows a laser micro-porator 10 comprising a laser source 7 and a laser beam shaping and guiding device 8. The laser source 7 comprises a laser pump cavity 7a containing a laser rod 7b, preferably Er doped YAG, an exciter 7c that excites the laser rod 7b, an optical resonator comprised of a high reflectance mirror 7d positioned posterior to the laser rod and an output coupling mirror 7e positioned anterior to the laser rod, and an absorber 7f positioned posterior to the laser rod. A focusing lens 8a and a concave diverging lens 8b are positioned beyond the output coupling mirror 7e, to create a parallel or quasi-parallel laser beam 4. The diverging lens 8b can be moved by a motor 8c in the indicated direction. This allows a broadening or narrowing of the laser beam 4, which allows changing the width of the laser beam 4 and the energy fluence of the laser beam 4. A variable absorber 8d, driven by a motor 8e, is positioned beyond the diverging lens 8b, to vary the energy fluence of the laser beam 4. A deflector 8f, a mirror, driven by an x-y-drive 8g, is positioned beyond the absorber 8d for directing the laser beam 4 in various directions, to create individual pores 2 on the skin 1 on different positions. The laser microporator 10 also comprises a control device 11, which connected by wires 11a with the laser source 7, drive elements 8c, 8e, 8g, sensors and other elements not disclosed in detail.

In a preferred embodiment the laser porator 10 also includes a feedback loop and feedback means. In FIG. 2, the feedback loop comprises an apparatus 9 to measure the depth of the individual pore 2, and preferably includes a sender 9a with optics that produce a laser beam 9d, and a receiver with optics 9b. The laser beam 9d has a smaller width than the diameter of the individual pore 2, for example five times smaller, so that the laser beam 9d can reach the lower end of the individual pore 2. The deflection mirror 8f directs the beam of the sender 9a to the individual pore 2 to be measured, and guides the reflected beam 9d back to the receiver 9b. In a preferred embodiment, the depth of the individual pore 2 is measured each time after a pulsed laser beam 4 has been emitted to the individual pore 2, allowing controlling the effect of each laser pulse onto the depth of the individual pore 2. The feedback loop 13 may, for example, comprise a sender 9a and a receiver 9b, built as a spectrograph 14, to detect changes in the spectrum of the light reflected by the lower end of the individual pore 2. This allows, for example, detecting whether the actual lower end 3a, 3b, 3c, 3d of the individual pore 2 is part of the stratum corneum 1a or of the epidermis 1b. The controller 11 also comprises a poration memory 12 containing at least specific data of the individual pores 2, in particular the initial microporation dataset. The laser porator 10 preferably creates the individual pores 2 as predescribed in the poration memory 12. The laser porator 10 also comprises one ore more input-output device 15 or interfaces 15, to enable data exchange with the porator 10, for example to enable the transfer of the parameters of the individual pores 2, the initial microporation dataset, into the poration memory 12, or to get data such as the actual depth or the total surface Ai of a specific individual pore 2i.

The pulse repetition frequency of the laser source 7 is within a range of 1 Hz to 1 MHz, preferably within 100 Hz to 100 kHz, and most preferred within 500 Hz to 10 kHz. Within one application of the laser porator 10, between 2 and 1 million individual pores 2 can be produced in the biological membrane 1, preferably 2 to 10000 individual pores 2, and most preferred 10 to 1000 individual pores 2, each pore 2 having a width in the range between 0.05 mm and 0.5 mm, and each pore 2 having a depth in the range between 5 μm and maximal 150 μm, but the lower end of the individual pore 2 being within the epidermis 1b.

The laser porator 10 also comprises an interlock mechanism, so that a laser pulse is emitted only when it is directed onto the biological membrane like the skin 1.

In a preferred embodiment the feedback loop 9 is operatively coupled to the poration controller 11, which, for example, can compare the depth of the individual pore 2 with a predetermined value, so that no further pulse of the laser beam 4 is directed to the individual pore 2 if the characteristic of the individual pore 2, for example, the depth, is greater than or equal to a preset value, or if the characteristic of the individual pore 2 is within a predetermined range. This allows quite accurately creating the depth of individual pores 2 with a predetermined depth. The feedback loop 9 may also be operated as a feed forward loop, to control the creation of new individual pores 2 based on data of already created individual pores 2. In a further embodiment, the laser beam 4 is operated as follows: If, for example, the measured depth is close to the value of the predetermined depth, the emitted energy per pulse of the laser beam 4 can be reduced, to create a pulse that ablates a smaller amount of tissue per pulse, so that the final depth of the individual pore 2 can be reached more accurate.

FIG. 2a shows a further embodiment of a laser microporator 10 comprising a controller 11, a single laser source 7 and optics 8 which guide the laser beam 4 into a plurality of fiberoptics 8h, thereby splitting up the laser beam 4 into a plurality of individual laser beams 4a, 4b, 4c, 4d. All fiberoptics 8h together form a deflector 8f, which directs the individual laser beams 4a, 4b, 4c and 4d in various directions. The exit end of each fiberoptics 8h has an individually oriented surface, such that the individual laser beams 4a, 4b, 4c, 4d leaving the fiberoptics 8h form an array of, for example, parallel individual laser beams 4a, 4b, 4c, 4d. The controller 11 comprises a poration memory 12, wherein at least an initial microporation dataset D can be stored. In the embodiment according to FIG. 2a, part of the initial microporation dataset D may be defined by the hardware of the laser micro-porator 10. For example the total amount of created pores per laser shot is defined by the number of fiberoptics 8h.

FIG. 3a shows an array of individual pores 2 in the skin 1, created by a micro-porator 10. In this example, all individual pores 2 have about the same shape and depth. The individual pores 2 may also have different shapes and depths, depending on the initial microporation dataset D.

FIG. 3b shows a plan view of the skin having a regular array of individual pores 2 that collectively form a micro-poration. The micro-poration on the biological membrane, after the laser porator 10 has finished porating, is called "initial microporation". The poration memory 12 contains the initial microporation dataset, which define the initial microporation. The initial microporation dataset comprises any suitable parameters, including: width, depth and shape of each pore, total number of individual pores 2, geometrical arrangement of the pores 2 on the biological membrane, minimal distance between the pores 2, and so forth. The laser porator 10 creates the pores 2 as defined by the initial microporation dataset D. This also allows arranging the individual pores 2 in various shapes on the skin 1.

Figure 3C:
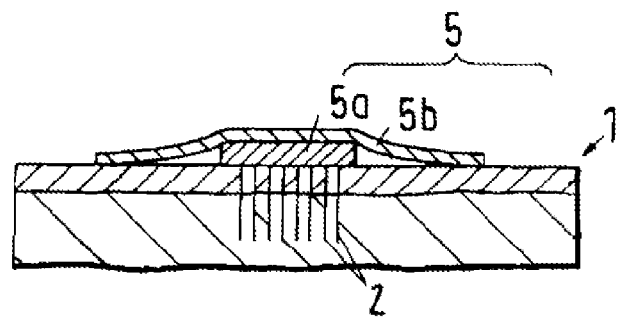
FIG. 3c shows a schematic cross-section of a porated skin with a drug container attached to the skin surface.

FIG. 3c discloses a transdermal patch 5 comprising a drug container 5a and an attachment 5b, which is attached onto the skin 1, the drug container 5a being positioned above an area comprising individual pores 2. The area can have a surface, depending on the number and spacing of the individual pores 2, in the range between 1 mm$^2$ and 1600 mm$^2$. Preferred 20×20 mm, e.g. a surface of 400 mm$^2$.

Figure 3D:
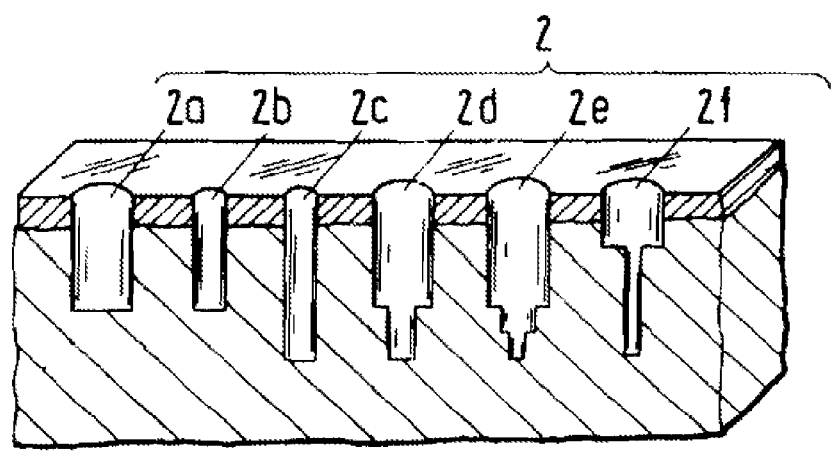
FIG. 3d-3e show examples of suitable shapes of microporations.
Figure 3E:
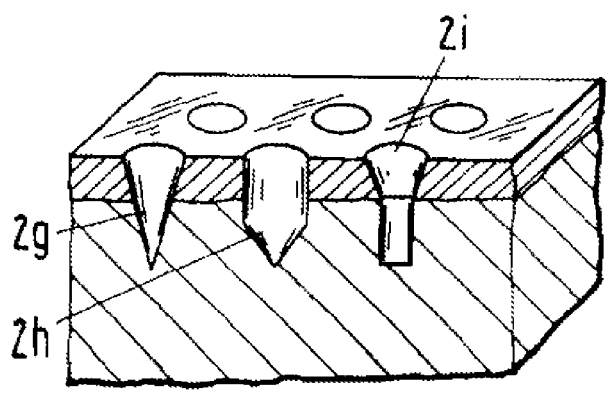

FIG. 3d shows individual pores 2a to 2f of various shapes, which can be created with support of the poration controller 11 controlling the laser porator 10. To produce the individual pores shown in FIG. 3d, at least the cross-section of the laser beam 4 has to be varied. In one embodiment, the laser porator 10 is able to vary the cross-section and/or the energy density of each consecutive pulsed laser beam 4, which allows creation of individual pores 2 with numerous different shapes. If the ablated layer per laser beam pulse 4 is very small, even conically shaped individual pores 2g, 2h, 2i, as disclosed in FIG. 3e, can be created. The shape of the pores 2g, 2h may also be created with a laser beam having an appropriate intensity distribution, such as disclosed in FIG. 3g.

The pores 2 created with the laser micro-porator may have other shapes than those disclosed in FIGS. 3a to 3e, depending on various factors such as beam shaping etc, so that, for example, the sidewalls of the micropores do not extend in parallel, as illustrated by pore 2g. The pores 2 disclosed in FIGS. 3a to 3e are more a schematic view, also not showing individual irregularities the pores 2 might have.

For each individual pore 2i, the surface of the inner wall and the surface of the lower end are of importance, in particular the permeation surface Ai, being the sum of both of these surfaces. In a preferred embodiment, the laser porator 10 comprises a distance measurement apparatus 9, which facilitates determining the permeation surface Ai very accurately. In a further preferred embodiment, the beginning of the epidermis is estimated by first determining the thickness of the stratum corneum. This in turn either permits determination of a corrected permeation surface Ai for each individual pore 2i, which establishes the effective permeation surface of the epidermis 1b, or which permits to increase the depth of the individual pore 2i by the thickness of the stratum corneum. This permeation surface Ai can easily be calculated for each individual pore 2i. If the individual pore 2i has the shape of, for example, a cylinder, the permeation surface Ai corresponds to the sum of $D*\pi*H$ and $(D/2)^2*\pi$, D being the diameter of the individual pore 2, and H being the total depth of the individual pore 2 or the depth of the individual pore 2 within the epidermis 1b. The effective permeation surface Ai in the pore 2 often doesn't correspond exactly to the geometrical shape, defined by D and H because the surface of the pore 2 may be rough or may comprise artefacts, which means the effective permeation surface is bigger than the calculated permeation surface Ai. The permeation surface Ai is at least a reasonable estimate of the effective permeation surface. Usually there is only a small or no difference between the permeation surface Ai and the effective permeation surface in the pore 2. The total permeation surface A of n individual pores 2i is then the sum A of all permeation surfaces Ai of all individual pores 2i.

Each individual pore 2 of the epidermis has a cell growth of usually 3 to 15 μm per day, the cells growing from the lower end of the individual pore 2 in direction Z to the stratum corneum 1a. This cell growth causes the permeation surface Ai of each individual pore 2i, respectively the total permeation surface A of all individual pores 2 to decrease in function of time. Depending on the total number of individual pores 2, which can be in a range of up to 100 or 1000 or 10000 or even more, the geometrical shape of the individual pores 2, and taking into account the effect of cell growth, the total permeation surface in function of time can be varied in a wide range. The initial permeation surface and also the decrease of the permeation surface over time can be predicted and calculated by an appropriate choice of the number of pores 2 and their geometrical shape. This definition of all pores is stored as the initial microporation dataset D. Correction factors may be applied to this initial microporation dataset D, for example based on user information like individual speed of cell growth, or based on the optional use of regeneration delayer like occlusive bandage, diverse chemical substances, etc., which influence the speed of cell growth.

Figure 3F:
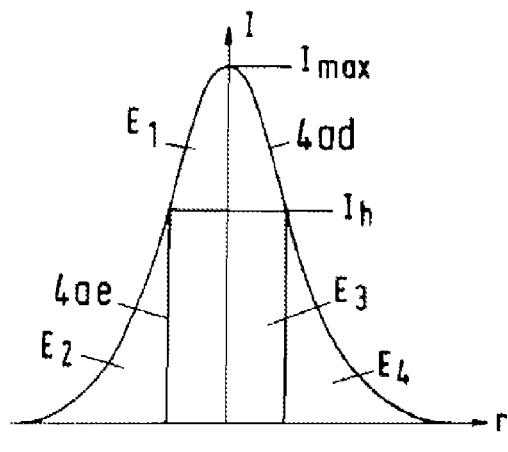
FIG. 3f shows schematically the intensity distribution of a beam without and with beam shaping.

FIG. 3f shows a laser beam 4ad with a Gaussian intensity distribution I in function of the radius r, the beam 4ad having a maximum intensity of $I_{max}$. Such a so called single mode laser beam is often used since it provides largest energy concentration, and for example creates deep holes. The effect of a laser beam shaping device that reshapes the energy intensity distribution of the laser beam 4 is schematically disclosed with a laser beam 4ae having a hard-edged and homogenous intensity distribution of intensity $I_h$. In reality these laser beams 4ad, 4ae are three-dimensional geometrical figures. The volumes of these figures have physical sense of energy of the laser beams 4ad, 4ae. E1,E2,E3 and E4 indicate different parts of the figures. These parts could be interpreted as parts of beam energy. E3 is the effective "cylinder" of energy and corresponds to the energy of the reshaped laser beam 4ae. E1 is an apex of Gauss function in an excess of energy over the intensity Ih of the reshaped laser beam 4ae. E1 is a loss of energy and also leads to bad effects regarding the shape of the created micropore. E2 and E4 are the tails of Gauss function that are losses of energy and also lead to bad effects, for example regarding the shape of the created micropore or regarding overheating of tissue. From the point of view of creating precisely shaped pores and/or saving energy to create pores and/or avoiding damages of the biological membrane, only the energy of part E3 is of interest, whereas the energy of parts E1, E2 and E4 are losses. In other word using a laser beam 4ad with a Gaussian intensity distribution when creating pores in a biological membrane has the effect that for example about 40% of the energy is effective to create the part E3, and for example about 60% of the energy is lost due to bad effects. Of course this example is based on the simplified geometrical interpretation based on FIG. 3f, but it clearly shows the effect of losses of laser energy, and it clearly shows the effect of using a beam shaping device that reshapes the energy intensity distribution of the laser beam. A usual laser source has a beam intensity distribution of a Gauss-function. The beam shaping device that reshapes the energy intensity distribution of the laser beam causes a hard-edged intensity distribution, which usually means a steeper slope on the side and/or a flat top, so that the profile shows a distinct edge. Very often a beam homogenizer is used to create an about homogeneous distribution, also called a flattop or a top-hat profile, having a shape close to a rectangle, as disclosed in FIG. 3h. This beam shaping can be provided by specially designed optical systems, for example so called homogenizers.

Figure 3G:
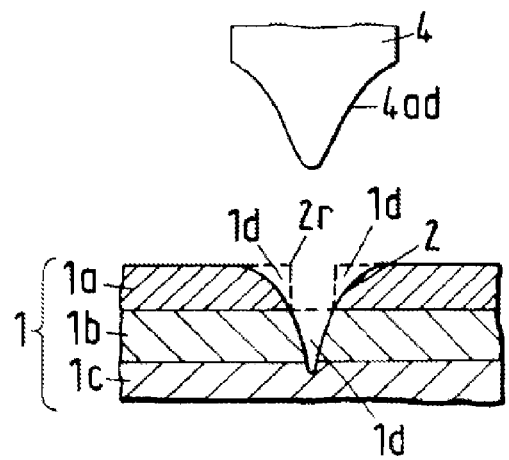
FIG. 3g shows a pore created without beam shaping.
Figure 3H:
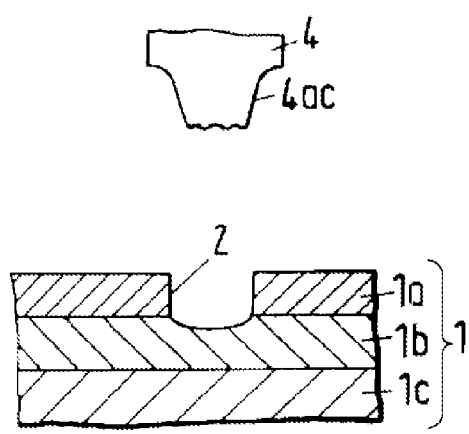
FIG. 3h shows a pore created with beam shaping.
Figure 3I:
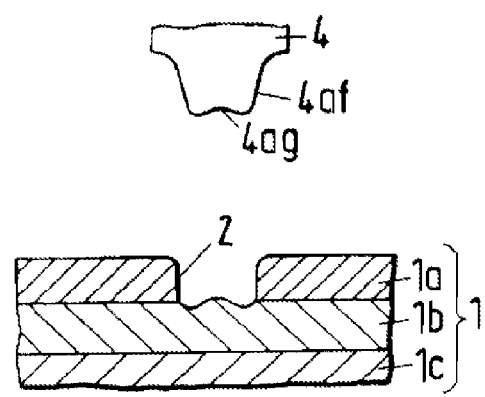
FIG. 3i shows a pore created with beam shaping

FIG. 3g shows a pore 2 in the skin 1 created with a beam 4 without beam shaping, the beam 4 has a Gaussian intensity profile 4ad. FIG. 3h shows a pore 2 in the skin 1 created with a beam 4 using beam shaping, beam 4 having a top hat intensity profile 4ac. The created pore 2 being cylindrical or almost cylindrical. FIGS. 3g also shows a dotted line 2r, which corresponds about to the shape of the pore 2 disclosed in FIG. 3h. Compared to the pore 2 created in FIG. 3g, the laser beam 4 applied in FIG. 3g ablates in excess a tissue volume marked with 1d, which also needs additional energy. Therefore, to create a pore 2 as disclosed in FIG. 3h needs less energy than the pore 2 disclosed in FIG. 3g. The pore disclosed in FIG. 3g has for example the further disadvantage that creating this pore 2 causes pain, in particular due to the fact the part of the dermis 1c is ablated. FIG. 3i shows a pore 2 in the skin 1 created with a beam 4 using beam shaping, the beam 4 having a top hat intensity profile 4af including a dip 4ag. The dip 4ag shows a decrease in the maximum energy of the beam 4. The dip may have up to 30% less energy than the maximum energy of the beam 4, preferably 10%, 20% or 30% less energy. Such an intensity profile 4ag is also called "donut profile". As disclosed the intensity profile 4af has also a hard-edged intensity distribution. A laser beam with a donut-profile has more energy on the periphery, which might lead to a more precise geometry of the inner wall of the crated pore 2.

FIG. 4 shows an example of a calculated total permeation surface A as a function of time. FIG. 4 shows the corrected total permeation surface A(t), which is the total permeation surface A(t) of the epidermis 1a only. The laser-porator 10 allows to micro-porating a biological membrane 1 by the creation of an array of micropores 2 in said biological membrane 1, whereby the number of micropores 2 and the shape of these micropores 2 is properly selected so that the sum of the micropores 2 forming an initial permeation surface, and that the permeation surface A (t) of the initial permeation surface decreases in a predetermined function over time, due to cell growth in the micropores 2.

The initial microporation dataset D according to FIG. 4 comprises three groups of cylindrical micropores 2 with different shapes:
  a first group consisting of 415 pores with a diameter of 250 µm, a depth of 50 µm and a permeation surface A1 as a function of time.
  a second group consisting of 270 pores with a diameter of 250 µm, a depth of 100 µm and a permeation surface A2 as a function of time.
  a third group consisting of 200 pores with a diameter of 250 µm, a depth of 150 µm and a permeation surface A3 as a function of time.

The total permeation surface A as a function of time is the sum of all three permeation surfaces A1, A2 and A3.

All individual pores 2i, which means the initial microporation, are created within a very short period of time, for example, within a time range of less than a second, so that beginning with the time of poration TP, the sum of all created pores 2i forming an initial permeation surface of 90 mm$^2$, which, due to cell growth, decreases as a function of time. At the time TC all individual pores 2i are closed, which means that the value of the permeation surface A becomes very small or zero.

Depending on the number of pores 2 and their shape, in particular the diameter and depth of the pores 2, the function over time of the total permeation surface A can be varied in a wide range. This makes it clear that the poration of individual pores 2 does not only determine the initial permeation surface, but also the function of the total permeation surface A over time. FIG. 4 shows the total permeation surface A over a time period of 9 days, starting with an initial permeation surface of 90 mm$^2$. The permeation surface A decreases within 9 days to a very small value or to zero. Depending on the shape of the individual pores 2, the time period may be much shorter, for example, just 1 day, or even shorter, for example, a few hours.

Figure 5A:
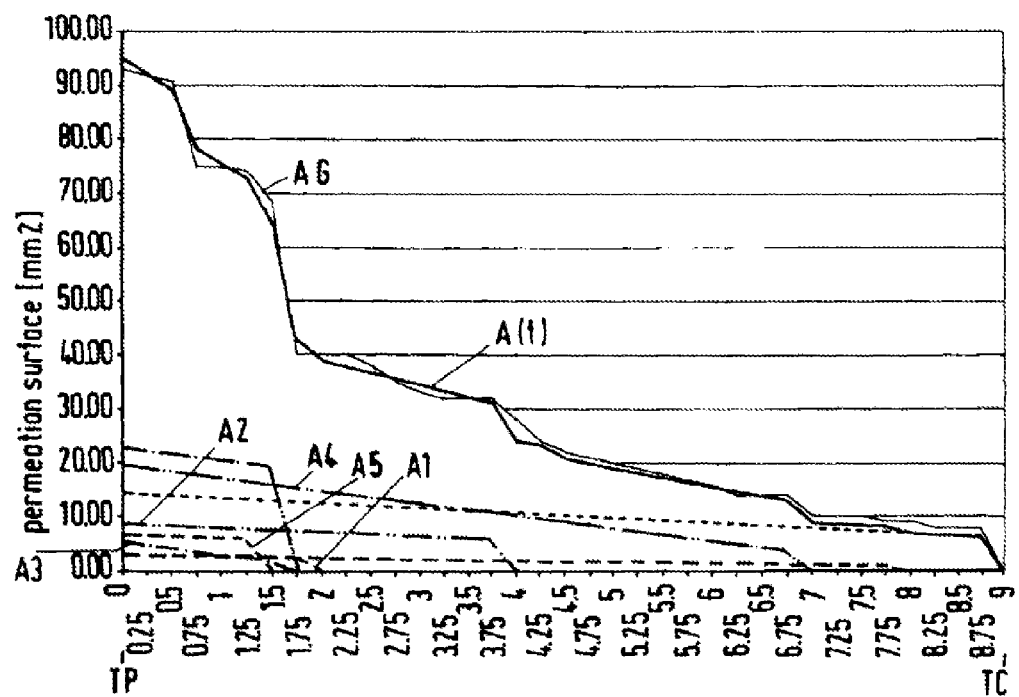
FIG. 5a shows a given permeation surface and a created permeation surface.

Almost any permeation surface A(t) as a function of time may be establish by a proper selection of the number and the shape of the individual pores 2. FIG. 5a shows a given function $A_G$ of a permeation surface as a function of time. FIG. 5a also shows the permeation surface of different groups A1, A2, A3, A4, A5, . . . of individual pores 2 over time. Each group being defined by a number of pores, a diameter and a depth. All individual pores 2 have cylindrical shape. By combining the individual permeation surfaces (A1, A2, A3, A4, A5, . . . ) of all the groups, a permeation surface A(t) is achieved, which function over time is quite similar to the given function $A_G$. The different groups of individual pores, their number and their shape can be determined by mathematical methods known to those skilled in the art. The definition of these groups is stored as the initial microporation dataset D.

Figure 5B:
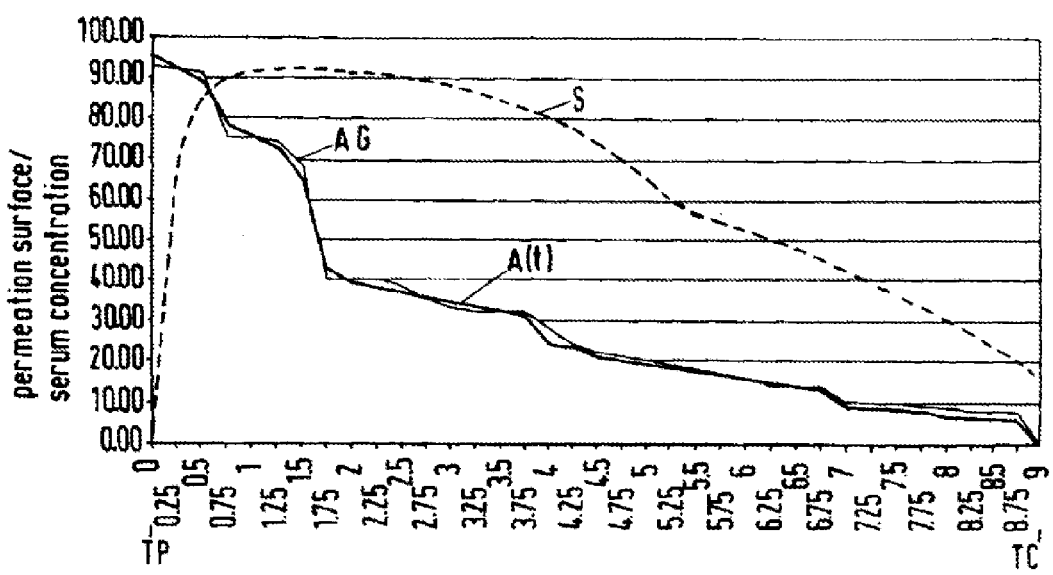
FIG. 5b shows transdermal delivery of a drug over time, in combination with a permeation surface.

FIG. 3c shows a patch 5 containing a drug 5a and being fixed onto the skin 1, above the individual pores 2. FIG. 5b shows the serum concentration S of this drug as a function of time in the blood. The drug is entering the permeation surface by passive diffusion. The amount of drug entering the permeation surface is mainly determined by the permeation surface A(t) over time, as long as the patch 5 provides a sufficient amount of drug. Preferably the patch 5 is able to provide much larger quantities of drug than the permeation surface A(t) is able to absorbe. Therefore, the serum concentration as a function of time can be determined by an appropriate poration of the skin 1 with an initial microporation.

Figure 6:
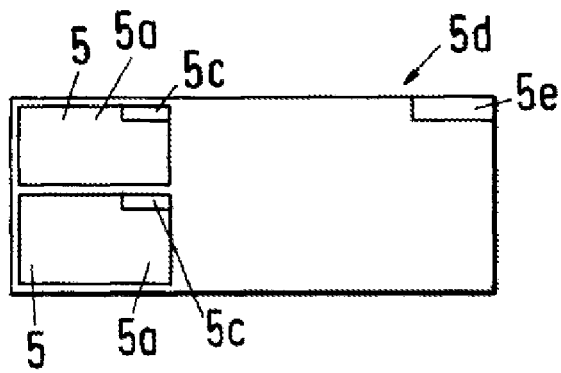
FIG. 6 shows a drug cassette containing two drug containers.

FIG. 6 shows a permeant 5a, which, for example, is a drug. The permeant 5a may be contained in a drug container 5 or a transdermal patch 5. The permeant 5a, the drug container 5 or the transdermal patch 5 comprises permeant information PI stored on a data carrier 5c. A plurality of permeants 5a, drug containers 5 or transdermal patches 5 can be stored in a cassette 5d. The cassette 5d can also comprise a data carrier 5e. The permeant information PI contains at least one data selected from the group: manufacturer ID, product ID, specific product ID, specific drug, drug concentration, nominal drug volume, drug container size, serial number, lot number, expiration date, initial microporation dataset D. The permeant information PI can also comprise information regarding doses, for example a minimal dose/day or a maximal dose/day. The permeant information PI can also contain the information of the entire patient information leaflet, including contraindications, therapeutically effective dosage, molecular weight, molecular size, polarity etc.

FIG. 2a shows a micro-porator 10 for porating a biological membrane 1, comprising: a controller 11, an initial microporation dataset D stored in the poration memory 12, and an ablator 10a for creating a microporation on the biological membrane 1, the controller 11 controlling the an ablator 10a based on the initial microporation dataset D, to create the microporation as defined by the initial microporation dataset D. The micro-porator 10 may be programmed with just one fixed initial microporation dataset D. This microporator 10 can, for example, be sold in combination with a specific drug. In a further embodiment, the data carrier 5c, can be inserted into the micro-porator 10, the data carrier 5c containing the initial microporation dataset D.

Figure 7:
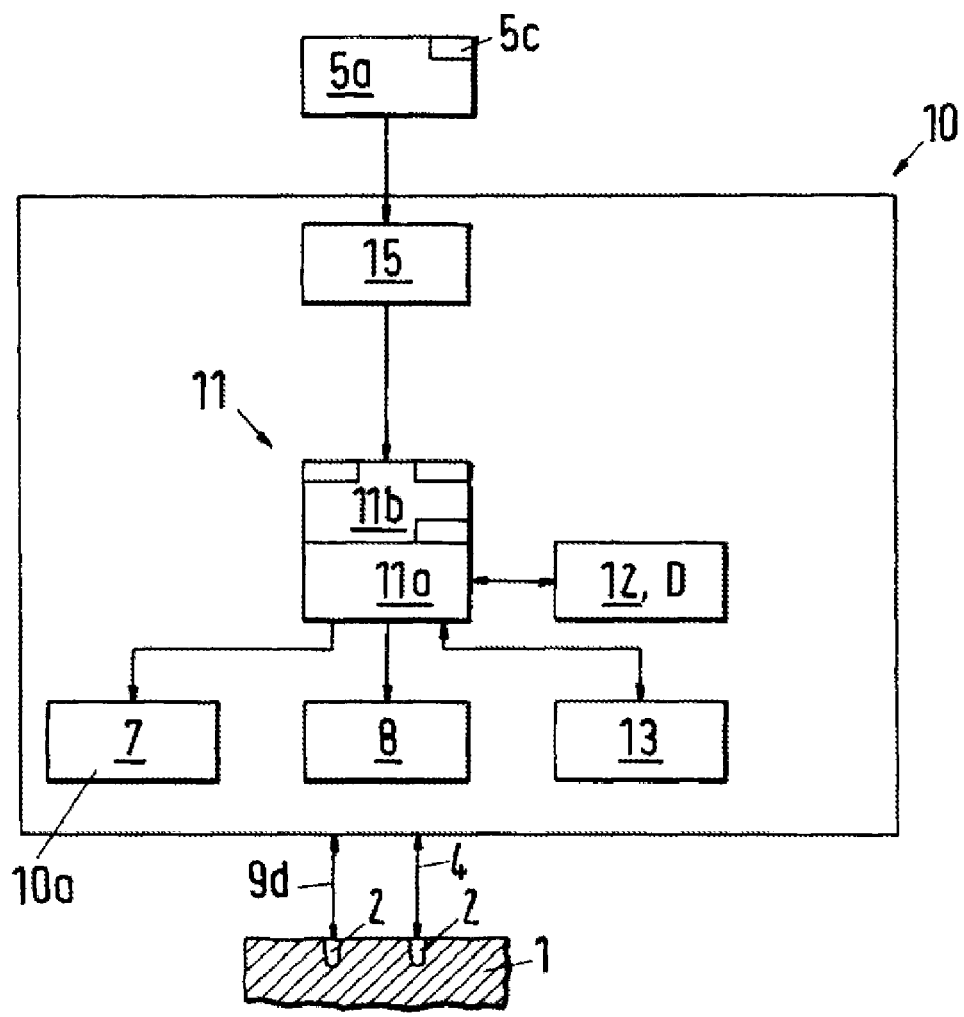
FIG. 7 shows a schematic view of a laser micro-porator.

FIG. 7 shows a micro-porator 10 comprising a controller 11, an interface 15, a poration memory 12, a laser 7, optics 8 and a feedback loop 13. The laser emitting a laser beam 4 to create pores 2 in the skin 1, and the feedback loop 13 emitting a laser beam 9d to measure the depth or other properties of the pores 2. The controller 11 contains a poration controller 11a which controls the laser 7 so as to create pores 2 as defined in the poration memory. The controller 11 also contains a main controller 11b which communicates with the poration controller 11a and the interface 15. The interface 15 allows reading at least one parameter selected from the group consisting of: permeant information PI, user information UI, initial microporation dataset D, porator application information PAI. The user information UI comprises data about the individual user such as sex, age, weight, body mass index, transdermal factors such as thickness of the stratum corneum, permeants which may or may not be used, maximal or minimal allowed dosage of drugs, or user ID. The porator application information PAI comprises information about how the porator is used, for example, at which time or date, for which user, for which drug etc. All data mentioned (PI, UI, D, PAI) may be stored on the data carrier 5c of the drug 5a. These data can, for example, be prescribed by a physician.

Figure 8:
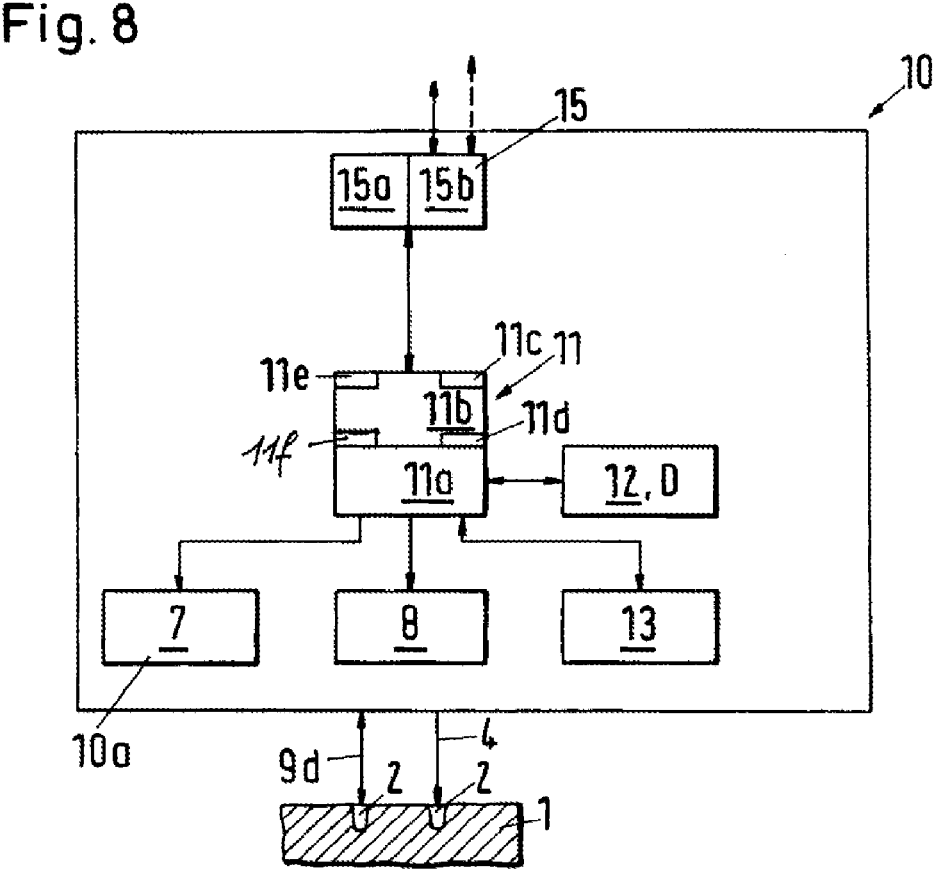
FIG. 8 shows a schematic view of a further laser micro-porator.

FIG. 8 shows a further micro-porator 10. In contrast to the embodiment disclosed in FIG. 7, the micro-porator 10 according to FIG. 8 has an interface 15 comprising a user-interface 15a to display data and to input data manually, and a data interface 15b to communicate date. The data interface 15b being able to communicate data selected from the group consisting of: 1-D, 2-D and 3-D bar codes, 1-D, 2-D and 3-D symbologies, holograms, written text, radio frequency identification devices (RFIDs), integrated chip smart cards, EEPROMs, magnetic strip, wire and wireless communication, USB-stick.

The controller 11 of the porator 10 can comprise an internal database 20 that stores a plurality of data of at least one parameter selected from the group consisting of: permeant information PI, user information UI, initial microporation dataset D, porator application information PAI. The database 20 may for example comprise two different initial microporation datasets D, each dataset defining the application of the same drug but with different speed, as disclosed in FIGS. 10a to 10b. The appropriate initial microporation dataset out of the two initial microporation datasets D may manually be selected by using a personalised adaptation system 11f, for example, based on the needs of the user. The personalised adaptation system 1 if may be also more sophisticated by taking into account user information UI. The system 11f will at least one of generate, select and modify the initial microporation dataset D to create a personalised initial microporation dataset D. The internal database 20 may also be stored on an external memory physically connected with the porator 10.

The controller 11 of the porator 10 may also comprise a selector 11d that automatically selects the most appropriate initial microporation dataset D out of a plurality of initial microporation datasets D. For example several initial microporation datasets D are stored in the internal database 20, taking into account different ages or different weights of users. Based on user information UI (for example age, weight), the most appropriate initial microporation dataset D is selected.

The controller 11 may also comprise an inhibitor 11c which inhibits the porator from porating when at least one of the following conditions is met: user information UI not correct, permeant information PI not correct, no valid initial microporation dataset D, user not allowed to apply the permeant, user not allowed to apply the initial microporation dataset D, user wants to apply the permeant outside a given timeframe (too early, too late), porator not directed onto the biological membrane. This inhibitor 11c allows a safe use of the microporator 10, or avoids a misuse of the microporator 10. The controller 11 can for example be used as a reminder to apply a drug, for example for elderly people who may forget applying an important drug. The controller 11 can be used to prevent suicide or addiction, in that the application of a certain drug is restricted, for example in time, in number or in amount. The controller 11 can be used to prevent the application of a wrong drug. The controller 11 can be used to prevent the application of a drug, for example, when the drug expired or when the drug, for certain reasons, may not be used any more.

The controller 11 of the porator 10 may also comprise a timer (11e) which recalls using the porator if it has not been used within a given period of time.

Figure 10A:
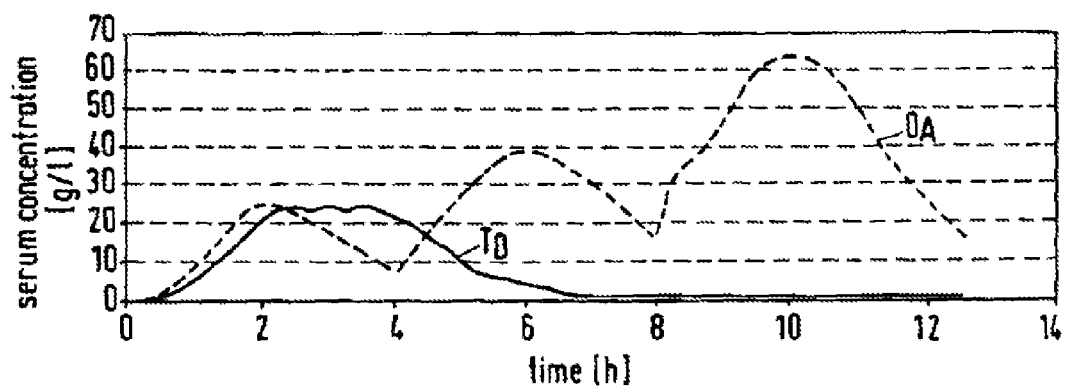
FIGS. 10a, 10b show the serum concentration of a drug over time, with the same amount of drug but different permeation surfaces.
Figure 10B:
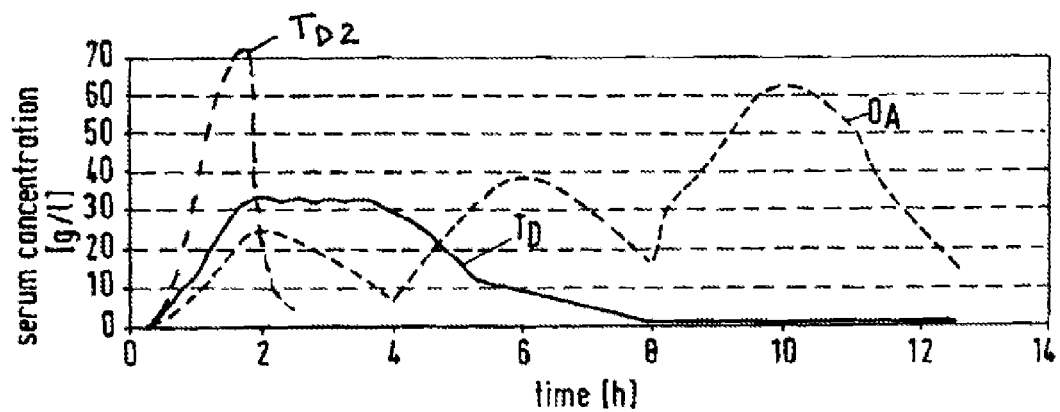

FIG. 10a to 10b show a hypothetical calculation of the administration of the same drug, for example 100 mg acetyl-salicylic acid, the drug being arranged on the skin 1 as disclosed in FIG. 3c. Depending on the permeation surface A(t) as a function of time, the level of the serum concentration as well as the time period within which the drug is released, can be predescribed. In FIG. 10a the permeation surface A(t), not shown in detail, is chosen such that the maximal serum concentration is about 25 g/l over a short period of time of about two hours. FIG. 10b shows a fast application (turbo) of the drug, with maximal serum concentration of about 30 g/l over a short period of time of about two hours. One advantage of the invention is, that with transdermal application TD the serum concentration reaches an about constant value, in contrast to oral application OA, which shows a heavy fluctuation. A further advantage is that the same amount of drug, e.g. the same patch, applied onto the skin 1, causes a different serum concentration, depending only on the function of the permeation surface A over time. This allows administering the same drug in different ways. This also allows administering the same drug in an individual way, in that the initial permeation surface is created depending on individual parameters of the person the drug is applied to.

The integrated permeant administering system comprises at least one permeant 5a, data of at least one initial microporation dataset D for the respective permeant 5a, and a microporator 10 for porating a biological membrane 1 as defined by the initial microporation dataset D. The micro-porator 10 comprises an interface 15 to read at least one parameter selected from the group consisting of: permeant information PI, initial microporation dataset D, user information UI, porator application information PAI. The permeant 5a comprises at least one parameter selected from the group consisting of: permeant information PI, initial microporation dataset D. The system can further comprise a database 20 with a plurality of initial microporation datasets Di for the same permeant 5a, the various microporation datasets Di relating to at least one parameter selected from the group consisting of: user information UI, amount of permeant absorption, time function of permeant absorption.

The system can consisting of a database 20 comprising permeant information PI for a plurality of different permeants, and comprising at least one initial microporation dataset Di for each permeant.

Figure 9:
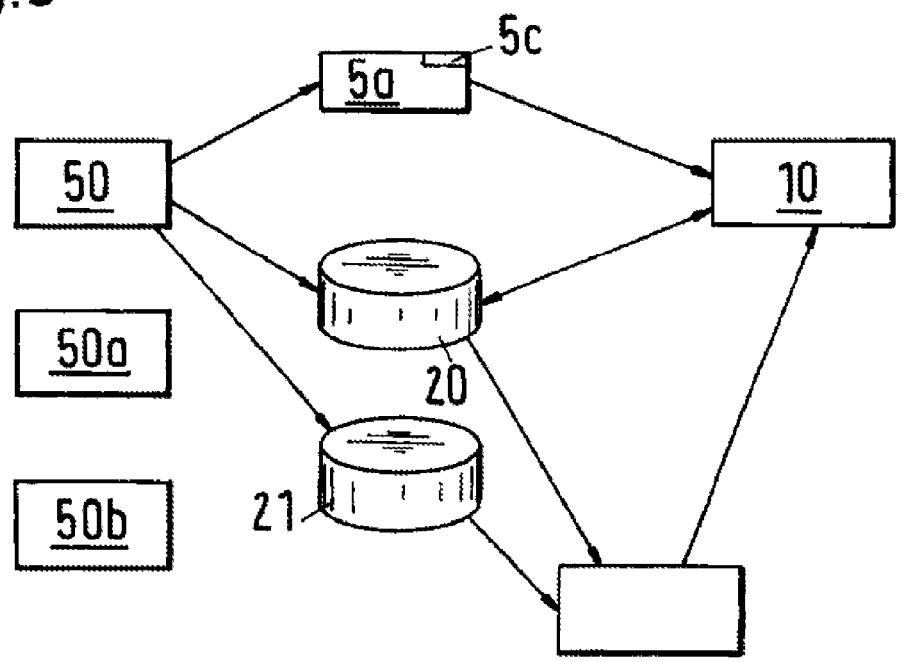
FIG. 9 shows a block diagram of an integrated drug administering system.

FIG. 9 shows a system comprising an external database 20, with which a plurality of micro-porators 10 can communicate. The micro-porator 10 can read the data carrier 5c of a permeant 5a. For each permeant 5a, at least one initial microporation dataset D is stored in the external database 20, so the porator 10 can get the initial microporation dataset D for every permeant 5a. For the data transfer, for example, a wireless communication is used.

In a preferred embodiment the database 20 is provided and/or updated by the company in charge for the permeant 5a, preferably pharmaceutical companies 50, 50a, 50b. These companies are in a position to provide the required data for combining a permeant 5a, for example a transdermal patch, with an appropriate initial microporation dataset D, to get an effective amount of permeant in the human body.

Also a physician may get access to the database 20 as well as to database 21 containing information regarding the permeant 5a. The physician may tailor an initial microporation dataset D, based on data of the databases 20, 21 and based, for example, on personalised needs of a patient, and prescribe this personalised initial microporation dataset D to the patient, and may transfer this personalised initial microporation dataset D to the micro-porator 10.

Figure 11A:
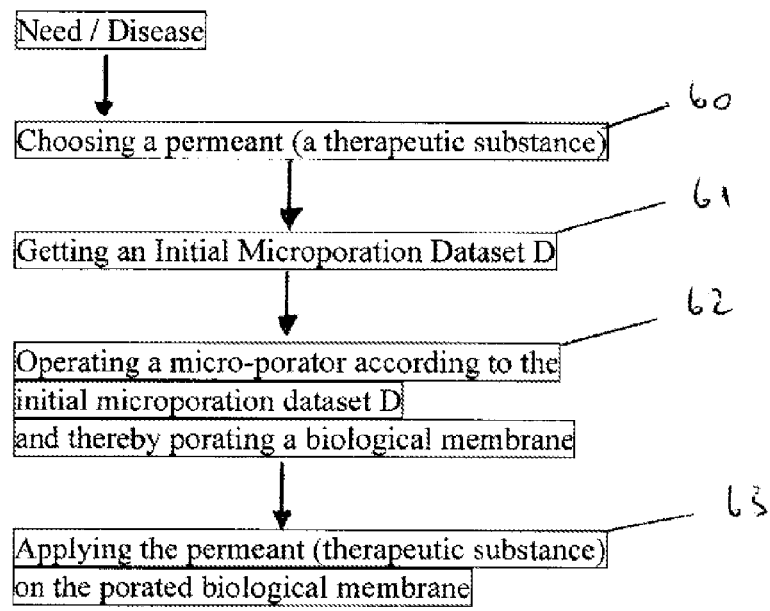
FIG. 11a to 11f show different methods for administering a permeant.

After determining the need or the disease of a person, the method for administering a permeant 5a with a micro-porator 10 comprises, as disclosed in FIG. 11a, the steps 60 of choosing a permeant 5a, the step 61 of getting an initial microporation dataset D for the respective permeant 5a, the step 62 of porating a biological membrane 1 as defined by the initial microporation dataset D, and the step 63 of applying the permeant 5a on the porated biological membrane 1.

This method if further explained by way of examples:

EXAMPLE 1

A drug 5a comprises a data carrier 5c with an initial microporation dataset D. This dataset is transferred to the micro-porator, which then creates the micropores. The drug 5a is then applied onto the porated area of the skin.

EXAMPLE 2

A drug 5a comprises a data carrier 5c with a plurality of initial microporation datasets D, for example three datasets D, one for slow, medium and fast application of the drug, as disclosed in FIGS. 10a to 10b. The user may, for example through the user interface 15a, select the appropriate initial microporation dataset D, according to which the micropores then are created.

EXAMPLE 3

A drug 5a comprises at least a specific drug-ID. The porator has access to an internal or external database 20 wherein initial microporation datasets D for a plurality of different drugs 5a are stored. The microporator 10 reads the specific drug-ID and retrieves from the database 20 the corresponding initial microporation dataset D, according to which the micropores then are created. The internal or external database 20 may be updated regularly, for example by data provided by pharmaceutical companies, so that the database 20 contains a library of an initial microporation datasets D for different drugs 5a. The library may contain further data, for example minimal dose/day, maximal dose/day etc. One advantage of this method is that the pharmaceutical company has direct influence to the administration of a drug. This makes the administration of the drug safer and also more efficient.

EXAMPLE 4

Figure 11B:
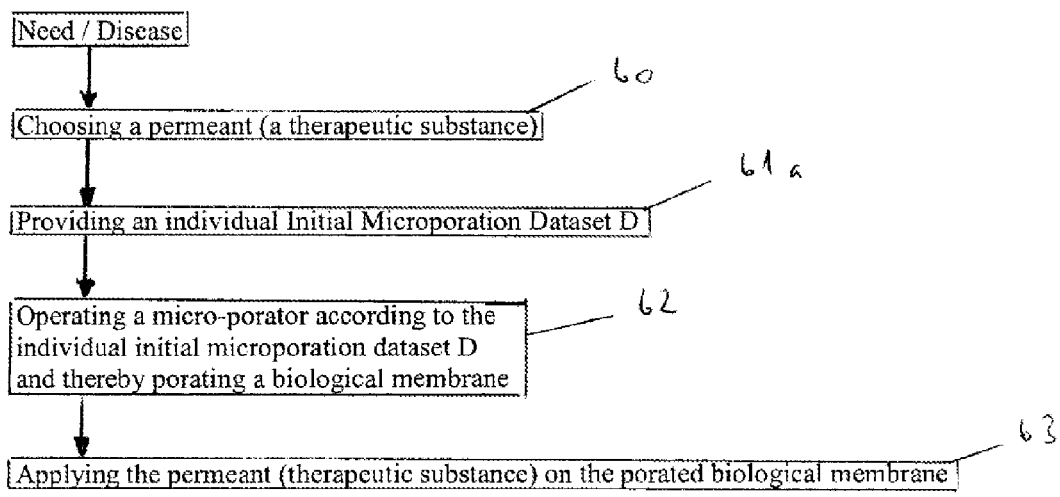

FIG. 11b discloses a further method for administering a drug 5a. In the first step 60 a drug 5a is chosen. A drug 5a comprises at least a specific drug-ID. The porator has access to an internal or external database 20 wherein initial microporation datasets D for a plurality of different personalised parameters like sex, weight, age or personalised restrictions are stored. In a next step 61a the microporator 10 reads the specific drug-ID, the microporator 10 reads the personalised parameters of the user and then retrieves from the database 20 the corresponding personalised initial microporation dataset D, according to which in step 62 the micropores then are created. In final step 63 the permeant 5a is applied on the porated biological membrane 1.

EXAMPLE 5

Figure 11C:
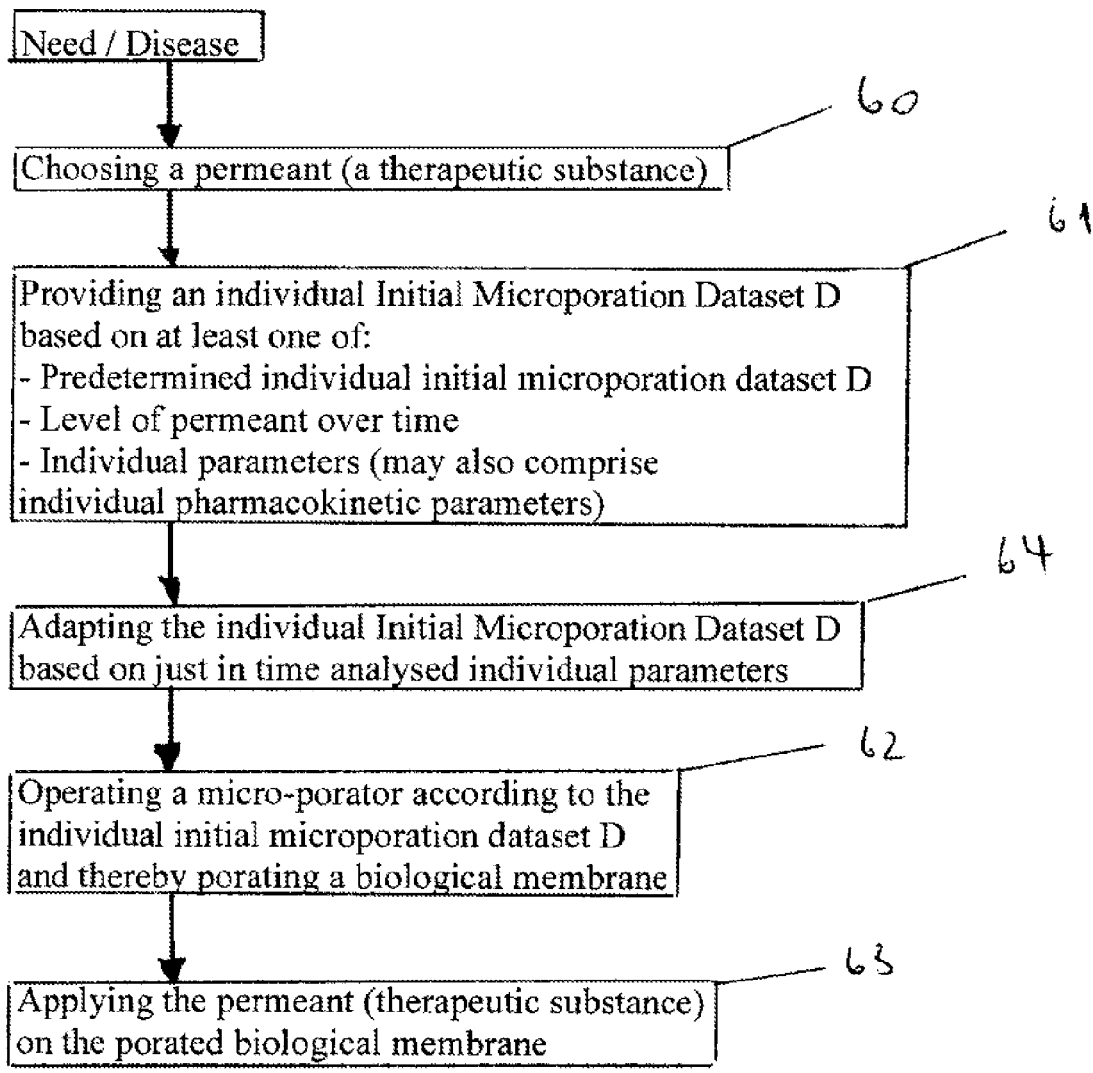

FIG. 11c discloses a further method for administering a permeant 5a. In the first step 60 a permeant 5a is chosen. In a second step 61 a personalised initial microporation dataset D is provided, based for example:

- on a personalised initial microporation dataset D which is predetermined for example by a physician for a specific individual.
- a desired level of a drug over time, for example as disclosed in FIG. 5b showing the serum concentration S in the blood over time. Starting with a desired level of a drug over time, for example the blood level, a personalised initial microporation dataset D is calculated or chosen. May be also an appropriate patch suitable to deliver the appropriate amount of drug is selected.
- Personalised parameters based on user information UI may be considered for providing an personalised initial microporation dataset D.

In a further step 64 the personalised initial microporation dataset D is adapted by personalised parameters which are measured just before porating the biological membrane. This parameters are called just in time analysed individual parameters JITAP, and may comprise for example day time of application, or personalised parameters such us blood pressure, weight, pulse rate, body temperature.

A specific example of the method disclosed in FIG. 11c may work as follows: A drug 5a comprises at least a specific drug-ID. A physician has access to a database 21 of various drugs 5a as well as to an external database 20 containing a lot of initial microporation datasets. Base on these data the physician may create a personalised initial microporation dataset D for a specific user. The physician may then create further personalised initial microporation datasets D1,D2,D3, taking into account just in time analysed individual parameters, like day time or body temperature. The microporator 10 reads the specific drug-ID, and the microporator 10 reads the personalised initial microporation datasets D, D2, D2, D3 created by the physician. Before the micropores are created, just in time analysed individual parameters JITAP are measures, for example the body temperature. This body temperature is transferred to the microporator 10, which with the selector 11c selects the most appropriate personalised initial microporation dataset D, according to which the micropores then are created.

Figure 11D:
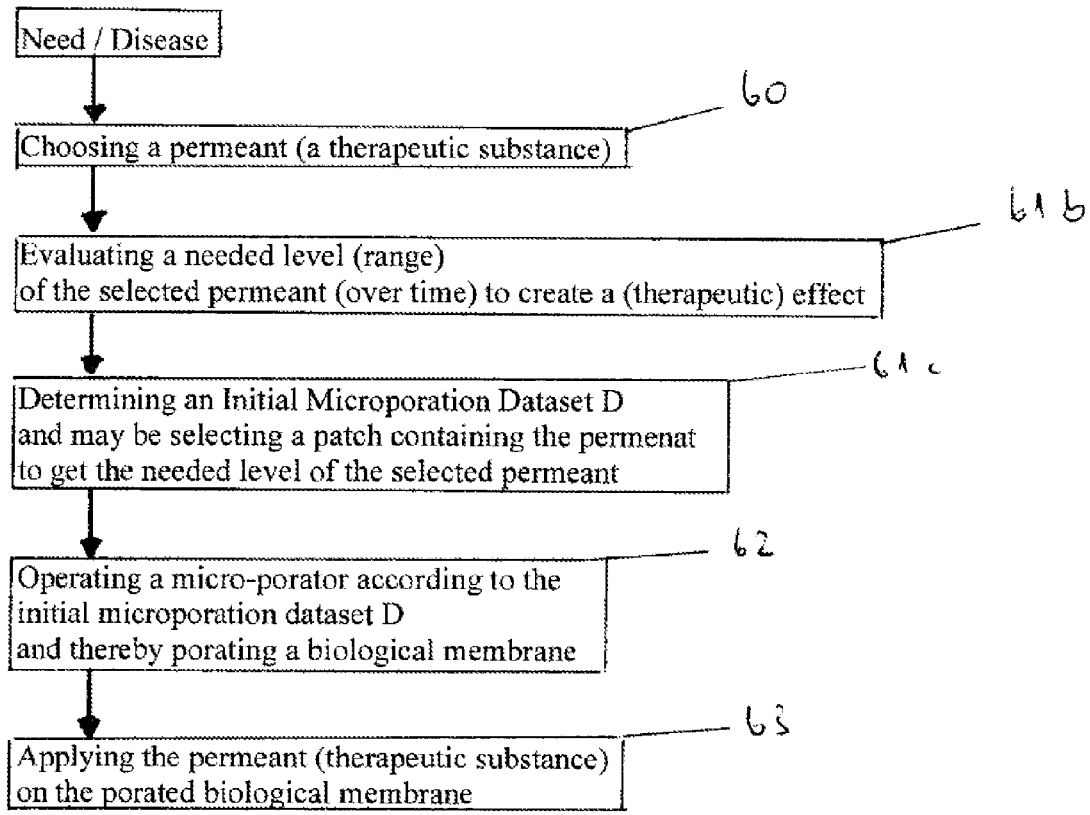
Figure 12:
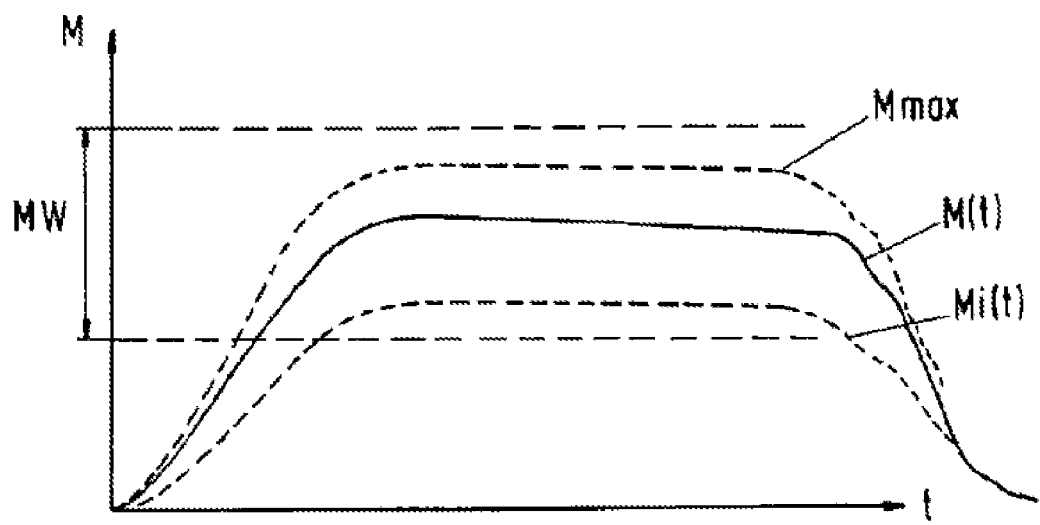
FIG. 12 a blood-level profile.
Figure 13:
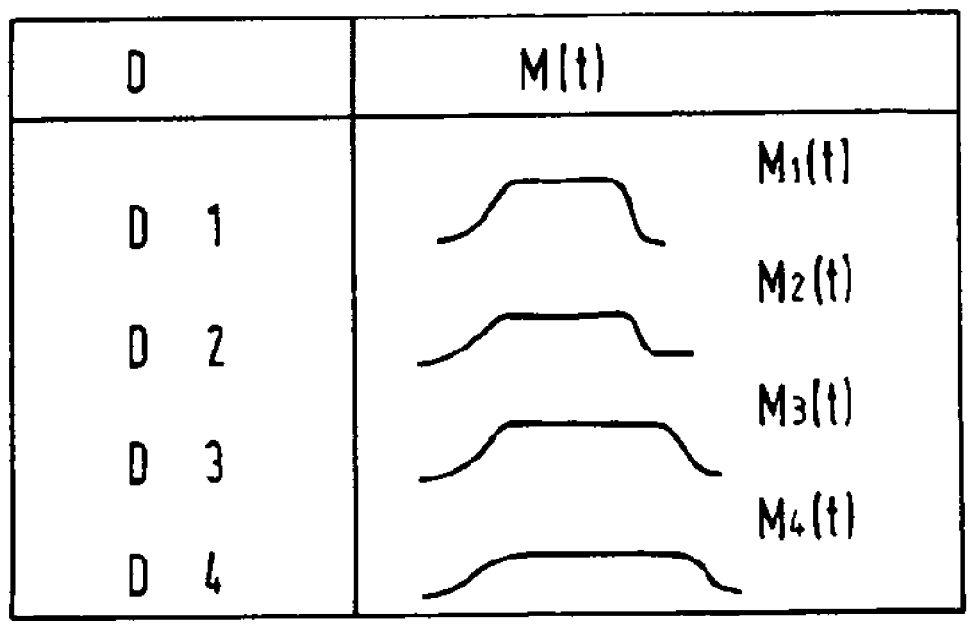
FIG. 13 table blood-level profiles and corresponding initial microporation datasets.

There are various other approaches about how to get data for the initial microporation dataset D. One approach would be to derive the initial microporation dataset out of a desired level or a level over time of the chosen permeant. FIG. 12 discloses a desired level over time M(t), which, for example, may be the serum concentration of the permeant in the blood of an individual person. Another approach may be to derive the initial microporation dataset D out of a desired maximal level Mmax, as disclosed in FIG. 12. FIG. 11d discloses such a method for administering a permeant 5a. In a first step 60 an appropriate permeant 5a is chosen, depending on the needs or the disease of the person. Based on the permeant information a maximal level Mmax or a level over time M(t) is defined in step 61b, which for example is done by a physician. Based on this date, in further step 61c the initial microporation dataset D is determined. Among different ways to determine the initial microporation dataset D, FIG. 13 shows one example, a table containing various predetermined levels over time M1(t) ... M4(t), and their corresponding initial microporation datasets D1 ... D4. Starting with the desired level over time M(t), the most appropriate predetermined level over time M1(t) ... M4(t) is selected, and by doing this, the corresponding initial microporation dataset D1 ... D4 is selected. The further steps 62 and 63 the micro-porator is operated according to the selected initial microporation dataset and the permeant is applied.

Very often when applying a permeant, in particular a drug, there is a so call therapeutic window, which means a range of for example a concentration level, within which the drug can create the desired effect. If the drug is applied in a concentration of too high or too low value, the desired effect doesn't take place, or even worse, an adverse effect is caused. In FIG. 12 an example of a therapeutic window TW is disclosed. One advantage of the method disclosed herein is, that a drug may be administered according to a needed amount, or an amount over time, or a concentration level, or a concentration level over time so that the permeant or drug is applied, in particular most of the time, within the therapeutic window TW, for producing a desired effect. The needed amount, amount over time, concentration level or concentration level over time determining the initial, or personalised initial microporation dataset D for the permeant 5a.

Figure 11E:
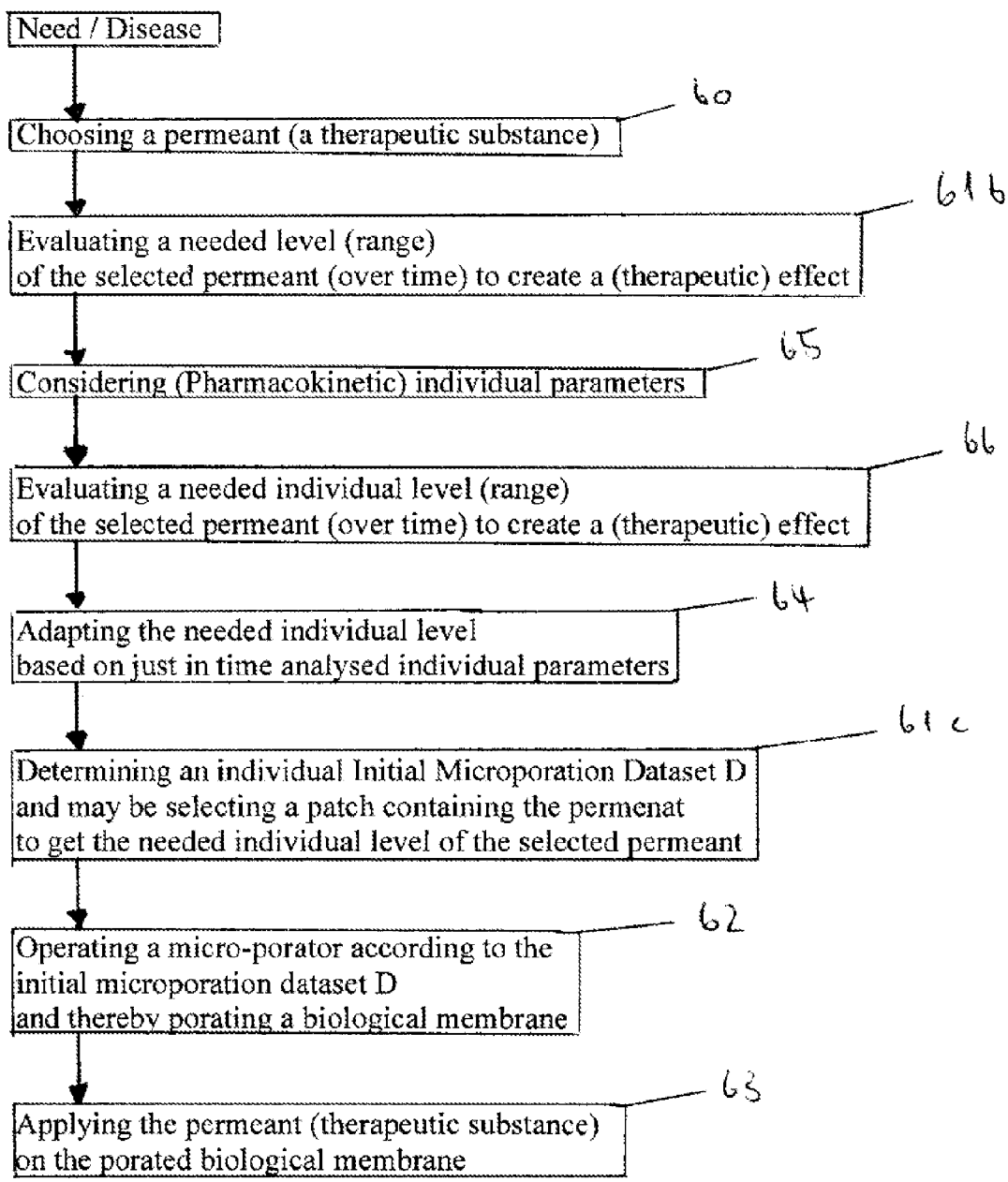

FIG. 11e discloses a further method for administering a permeant 5a, which considers personalised parameters, in particular individual pharmacokinetic parameters. The first two steps 60 and 61b are the same as those disclosed in the method according to FIG. 11d. After knowing the desired value of M(t) or Mmax, individual effects are considered in next step 65 such as individual user information UI like sex, age, or weight. In a more sophisticated approach, detailed individual pharmacokinetic parameters are considered, which might influence the desired value of M(t), which might be the serum concentration of the permeant in the blood of the individual person. The individual pharmacokinetic parameters may comprise at least one of: basic metabolism values, thyroid gland values, adrenal gland values, age, sex, weight, size, skin surface area, body temperature, renal function parameters, clearance, creatinine, liver function parameters, bilirubin, GOT, γ-GT, lung function parameters, cytochrome P450, hydrolases, esterases, peroxidases, monoamine oxidases, alcohol hydrogenases, aldehyd hydrogenases, drug anamnesis, interactions, food anamnesis, glucoronidation, acetylation, glutathion conjugation, skin humidity, TEWL (trans epidermal water loss), body fat, incompatibilities, allergy (atopies) and others.

Taking into account the information of step 65, in successive step 66 a needed individual level M(t) of the permeant can be evaluated. Step 66 considers at least one of the following effects:

the needed individual level Mi(t) considering individual parameters, to reach the desired therapeutic effect. As disclosed in FIG. 12, the individual level Mi(t) might be larger or smaller than the needed level M(t).

the individual effect of the diffusion of the permeant into the biological membrane. Depending on individual parameters like thickness of the stratum corneum or skin humidity, the amount of permeant which enters the skin or which enters the blood may vary. This effect has to be taken into account to by the end getting an individual level M(t), for example in the serum.

In a successive step 64, just in time analysed individual parameters JITAP may be considered, as describe in FIG. 11c, to further adapt the needed individual level M(t).

In step 61c, a personalised initial microporation dataset D is determined, and in addition an appropriate patch containing the permeant may be selected, to get the needed personalised level M(t). In step 61c a table as disclosed in FIG. 13 may be used to get the values of the personalised initial microporation dataset D. Steps 62 and 63 are the same as disclosed in FIGS. 11a-11d.

In step 61c, the personalised initial microporation dataset D can be determined by various different methods. For example a computer model may be used, which could be based on formulas, statistical models, measured data or neuronal networks, and which could consider permeant information PI or user information UI, to for example calculate the initial total permeation surface A and the total permeation surface over time A(t).

Figure 11F:
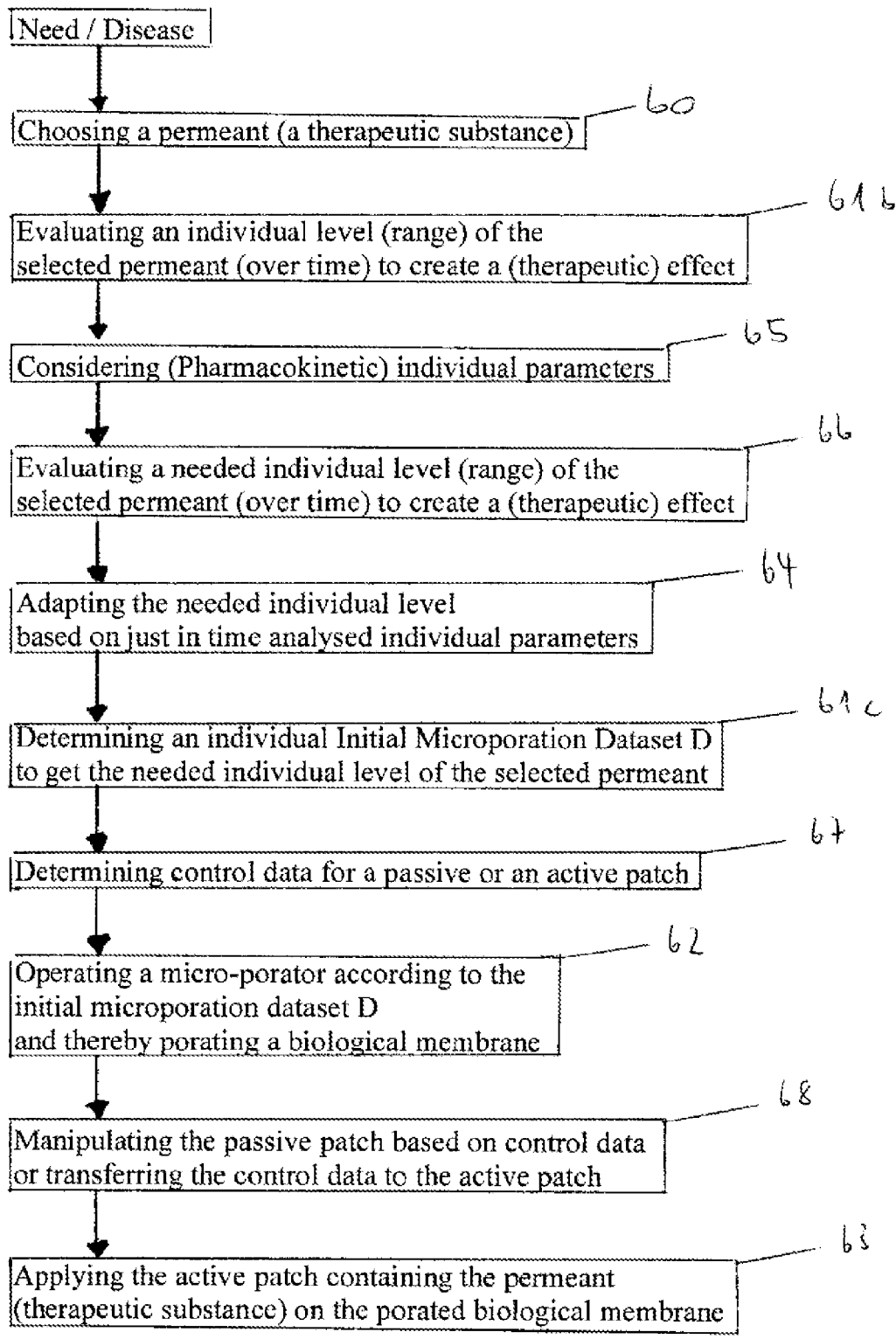

The method disclosed in FIG. 11e preferably uses a standard passive patch which delivers the permeant 5a by passive diffusion. In a further method disclosed in FIG. 11f in detail, the patch is an active or passive patch, which, before applying onto the porated biological membrane, may be modified or manipulated, to for example increase the flux rate of the permeant 5a. The membrane of a passive patch may for example be porated to create or widen membrane wholes, and to increase the flux rate. The membrane of the passive patch may be porated by using the micro-porator or by using other means. Also an active patch, for example comprising controlled vales or pumps, may be used. In addition to the method disclosed in FIG. 11e, the method according to FIG. 11f also comprises a step 67 for determining data about how to modify a passive patch, or about how to control an active patch. The method according to FIG. 11e further comprises step 68 for manipulating the passive patch or for transferring control data to the active patch.

In a further method for administering permeants, at least two different permeants may be administered, the method comprising the steps of:

choosing at least two different permeants 5a1,5a2,
getting an initial microporation dataset D1,D2 for each of the permeants 5a1,5a2,
porating the biological membrane 1 on separate locations and as defined by the initial microporation datasets D1,D2, and
applying the permeants 5a1, 5a2 on the respective location.

The same micro-porator 10 can be used to sequentially create micropores, first according to dataset D1 and afterward according to dataset D2. This method allows administering a plurality of different permeants at the same time or also at different time.

These were only examples of a wide variety of possibilities about how to administer a permeant like a drug with the integrated permeant administering system according to the invention.

The database 20 can also be arranged within the micro-porator 10. This database 20 can regularly be updated, for example by use of a serial or parallel interface, or by use of a wireless link like GSM (Global Systems for Mobile Communications), SMS or Bluetooth, by access to the internet, by access to a docking station, for example in a drug store, or by a physical data carrier.

The transdermal delivery system for treating infertility in a patient comprises an apparatus for facilitating transdermal delivery of a drug through an area of the skin of the patient, wherein the apparatus comprises an ablator that is configured to generate a microporation in the area of the skin of the patient, and comprising a drug (5a), wherein the drug effects at least one of the biological regulation of at least one oocyte containing follicle, stimulation of follicle growth, induction of ovulation, promotion of gestational status, maintenance of conceptus, maintenance of pregnancy.

The method of treating infertility in a patient comprises administration of a plurality of drugs to effect at least one of regulation biological activity relating to the fertility cycle, stimulation follicle growth, induction of ovulation, promotion gestational status, maintenance of conceptus, maintenance of pregnancy, wherein at least one of the plurality of drugs is administered transdermally by at least one of a medically trained professional and patient using poration.

In a preferred embodiment, the transdermal delivery system comprising data of at least one initial microporation dataset D for the drug 5a, and the apparatus 10 configured to porate the skin 1 as defined by the initial microporation dataset D.

In a preferred embodiment, the transdermal delivery system the apparatus comprises a personalised adaptation system 11f, which, by taking into account user information UI, will at least one of generate, select and modify an initial microporation dataset D.

In the most preferred embodiment the transdermal delivery system comprises an apparatus with a laser, a deflector and a control unit which is adapted to apply the laser to form a plurality of micro-pores in the skin. Most preferred, the control unit is adapted to vary at least one of shape, position and number of the plurality of micro-pores, to achieve a poration with a plurality of pores, preferably to reach a predetermined drug delivery characteristic.

In an advantageous method step, at least one of GnRH-agonists (for example Triptorelin), Follicle stimulating hormone (FSH), Human chorionic gonadotropin (HCG), Luteinizing hormone (LH) and Progesterone is administered.

An example of a known stimulation protocol for recruitment of multiple healthy fertilizable oocytes for the purpose of in vitro fertilization (IFV) which uses intramuscular injection of the listed drugs is disclosed in table 1.

TABLE 1

| Day number | Drug name | Dosage | Agent |
|---|---|---|---|
| 1-22 | Decapeptyl ® | 0.1 mg | Triptorelin, GnRH-agonist |
| 10-21 | Menopur ® 75 IU | 75 IU LH, 75 IU FSH | LH and FSH |
| 10-21 | Gonal ® F 150 IU | 150 IU FSH | rec FSH (Follitropin alpha) |
| 22 | Pregnyl ® 5000 IU | 5000 IU | Human Choriongonadotropin HCG |
| 23-30 | Gestone ® | Alternating day 50 mg and 100 mg per day | Progesteron |

Starting with day number 1, the agent GnRH-agonist (Triptorelin), for example Decapeptyl® is injected once a day, during 23 days, with a dosage of 0.1 mg. Starting with day 10, and during days 10 to 21, the agents LH and FSH, using two different drugs, for example Menopur® 75 IU and Gonal® F 150 IU is injected once a day. On day 22 Pregnyl® is injected. On Days 23 to 30, the agent Progesteron (Gestone®) is injected. Table 1 is just an example of an individual stimulation protocol out of a plurality of different stimulations protocols. Such stimulation protocols may for example vary in the agents that are administered, or it may for example differ in the number of days the agents are administered. It may be the case that also only one single agent is administered.

According to the invention, preferably the poration is performed such as to allow administration, in particular sustained administration, as for example disclosed in FIG. 12, of at least one of GnRH-agonist (Triptorelin), Follicle stimulating hormone (FSH), Human chorionic gonadotropin (HCG), Luteinizing hormone (LH) and Progesterone over a predetermined period of time.

In an advantageous method step Human chorionic gonadotropin (HCG) is transdermally administered.

In a further advantageous method step the poration is performed such as to allow administration of Human chorionic gonadotropin (HCG) so that a bioavailability at a desired dose level is reached within less than two hours. Such an application is disclosed in FIG. 10b.

In a further advantageous method step at least one of a plurality of drugs is administered at a first location, and wherein a further of the at least one of a plurality of drugs is administered at a different location on the skin. According to the protocol of table 1, Menopur® and Gonal® may be applied on different locations on the skin.

In a further advantageous method step at least two of the drugs GnRH-agonist (Triptorelin), Follicle stimulating hormone (FSH), Luteinizing hormone (LH), Human chorionic gonadotropin (HCG) and Progesterone are administered during an overlapping period of time. According to the protocol of table 1, Decapeptyl® as well as Menopur® and Gonal® are administered in overlapping time periods.

In a further advantageous method step at least one of the plurality of drugs is administered using a patch, for example as disclosed in FIG. 3c. Most preferably a medical patch comprising the drug or the pharmaceutical composition is used, optionally comprising also penetration enhancers. The pharmaceutical composition is formulated in a form selected from the group consisting of a powder, a solution, a gel or a hydrogel. The medical patch preferably comprising a layer selected from a backing layer, an adhesive and a release liner.

In a further advantageous method step the patch comprises an amount of the drug, wherein the amount of the drug is greater than the amount that is administered to the patient.

In a further advantageous method step predetermined poration parameters determine the administered dosage, for example as disclosed in FIGS. 5a, 10a, 10b or 12 or method steps according to FIGS. 11a to 11f.

In a further advantageous method step the poration parameters are determined according to the patients personal characteristics, for example based on user information UI.

In a further advantageous method step progesterone is transdermally administered in an amount of up to 500 mg/day.

In a further advantageous method step progesterone is administered during a period of time between 2 weeks and 9 months, for example by applying one patch per day.

In a further advantageous method step follicle stimulation hormone (FSH) is transdermally administered in an amount between 150 IU/day and 250 IU/day or in an amount between 25 IU/day and 600 IU/day.

In a further advantageous method step, the surface of the ablated skin or membrane is about two to ten times smaller than the total surface of the created pores.

The transdermal delivery system as well as the method of treating infertility according to the present invention allows administering the drug with a more constant value, as disclosed in FIG. 10a by TD. Administering the drug by injection, for example intramuscular injections, results in a drug concentration as shown by OA. As disclosed in FIG. 12, at least some of the drugs administered need to reach a certain minimum level to have a therapeutic effect, which means the concentration has to be within the therapeutic window TW. For some drugs the concentration has only to exceed the lower end of the therapeutic window TW to be therapeutic active, whereas there is no upper limit. The method according to the invention has not only the advantage that it is painless, injection free and has no gastrointestinal tract interference, but allows systemic delivery, even with higher dosage rates. It was found out that a proper dosage of the drugs is crucial regarding the success rate in treating infertility. The method according to the invention allows administering the drug more precisely and preferably also during a longer period of time within the therapeutic window TW. Therefore the drugs are therapeutically available for a longer period of time. By the option of using an initial microporation dataset when creating the pores, the serum level may even be more precisely influenced. This also allows for example using a patch containing a standard concentration and determine or influence the serum level by the pores created, which means individually tailoring the dose or serum level. The method according to the invention for treating infertility has also the advantage that it leads to higher success rate. The method has the further advantage that the total amount of drugs needed may be reduced, because of the precise dosage. Therefore the treatment becomes cheaper, in particular if expensive drugs such as FSH are used. The higher cost for recombinant products limits their use in IVF up to now. The method according to the invention lowers costs and increases success rates.

A further advantage is that a lower total amount of drugs is applied. Therefore the method has lower side effects. The method has the further advantage that the drug delivery may be interrupted at any time by removing the patch, even by the patient. This may be of particular importance after the onset of an Ovarian hyperstimulation syndrome (OHSS). Removing the patch allows to immediately terminate drug delivery. If several patches with different drugs are used simultaneously, specific patches may be removed, leaving the others attached on the skin to continue drug delivery.

Most preferred, the dosage of drugs for treating infertility is individually determined, depending on individual factors of the subject. These factors may be physiological factors, for example weight or body index, or transdermal factors, for example thickness of the stratum corneum. Based on this information for example the initial microporation dataset may be generated, to individually porate the skin and to therefore individually tailoring the dose of drug. The Patch is applied onto the pores after porating the skin.

A advantageous method comprises marketing of a poration device, comprising a step of providing information that the device is used by a patient to administer a drug for infertility treatment.

A kit for treating infertility in a patient comprises
a) a patch containing a drug and
b) a device for poration of the skin, wherein the device is not a syringe, and wherein the device is most preferably a laser.

In the kit the patch may also comprising two separate compartments containing two different drugs.

All details regarding poration, poration devices, systems to create porations and so on are disclosed in the citations, which are incorporated by reference in their entirety.

It should be especially appreciated that the apparatus 10 described herein is configured to generate a plurality of micropores, preferably with individually predetermined geometries, in a biological membrane such as the skin. Therefore, it should be recognized that such apparatus may not only be used for treating infertility but may also be used independently in applications where microporation, and particularly microporation with predetermined drug delivery kinetic/dynamic is required. For example, contemplated alternative uses include application of other permeants and drugs such as psychoactive drugs, antibiotics, etc.

The invention claimed is:

1. A method of treating infertility in a patient, comprising:
administering at least one drug to have at least one of the following effects selected from the group consisting of: stimulation of follicle growth, induction of ovulation, promotion of gestation, maintenance of conceptus, and maintenance of pregnancy,
wherein the at least one drug is administered transdermally to a site of laser poration having a predetermined permeation surface over time, wherein the predetermined permeation surface over time is effective to achieve a predetermined serum concentration of the at least one drug to thereby treat the infertility, further wherein the site of laser poration comprises a plurality of pores having different geometries,
wherein the step of administering the at least one drug to the patient in need thereof is performed by at least one of a medically trained professional and a patient, and
wherein the at least one drug is selected from the group consisting of a GnRH agonist, a follicle stimulating hormone (FSH), a human chorionic gonadotropin (hCG), a luteinizing hormone (LH), and a progesterone.

2. The method according to claim 1, wherein the GnRH agonist, the FSH, the LH, the hCG, and the progesterone are administered.

3. The method according to claim 2, wherein the poration is performed such as to allow sustained administration of the at least one of the GnRH agonist, the FSH, the hCG, the LH and the progesterone over a predetermined period of time.

4. The method according to claim 1, wherein the hCG is transdermally administered.

5. The method according to claim 4, wherein the site of laser poration allows administration of the hCG so that a bioavailability at a desired dose level is reached within two hours or less.

6. The method according to claim 1, wherein at least one drug is transdermally administered at a first location, and wherein a further of the plurality of drugs is transdermally administered at a different location.

7. The method according to claim 1, wherein more than one drug selected from the group consisting a GnRH agonist, FSH, LH, hCG and progesterone is administered, and wherein at least two of said drugs are administered during an overlapping period of time.

8. The method according to claim 1, further comprising a step of administering at least one drug using a patch.

9. The method according to claim 8, wherein the patch comprises an amount of at least one drug, wherein the amount of at least one of the plurality of drugs is greater than a quantity that is absorbable by a permeation surface formed in the patient.

10. The method according to claim 1, wherein the predetermined permeation surface over time is determined according to the patient's personal characteristics.

11. The method according to claim 1, wherein progesterone is transdermally administered in an amount of up to 100 mg/day.

12. The method according to claim 1, wherein progesterone is administered during a period of time between 2 weeks and 9 months.

13. The method according to claim 1 wherein the FSH is transdermally administered in an amount between 150 I.U./day and 250 I.U./day.

14. The method according to claim 1 wherein the FSH is transdermally administered in an amount between 25 I.U./day and 600 I.U./day.

15. The method according to claim 1, wherein the site of laser poration includes a plurality of pores.

16. The method according to claim 1, wherein a surface of ablated skin or membrane in the patient is about two to ten times smaller than a total inner surface of pores created by the laser poration.

\* \* \* \* \*